(12) United States Patent
Miles et al.

(10) Patent No.: US 10,253,028 B2
(45) Date of Patent: Apr. 9, 2019

(54) PYRAZOLO[3,4-D]PYRIMIDIN DERIVATIVE AND ITS USE FOR THE TREATMENT OF LEISHMANIASIS

(71) Applicants: GlaxoSmithKline Intellectual Property Development Limited, Brentford (GB); University of Dundee, Dundee (GB)

(72) Inventors: Timothy James Miles, Madrid (ES); Michael George Thomas, Dundee (GB)

(73) Assignees: GlaxoSmithKline Intellectual Property Development Limited, Brentford, Middlesex (GB); University of Dundee, Dundee (GB)

(*) Notice: Subject to any disclaimer, the term of this patent is extended or adjusted under 35 U.S.C. 154(b) by 0 days.

(21) Appl. No.: 15/545,193

(22) PCT Filed: Jan. 21, 2016

(86) PCT No.: PCT/EP2016/051240
§ 371 (c)(1),
(2) Date: Jul. 20, 2017

(87) PCT Pub. No.: WO2016/116563
PCT Pub. Date: Jul. 28, 2016

(65) Prior Publication Data
US 2017/0369496 A1 Dec. 28, 2017

(30) Foreign Application Priority Data
Jan. 23, 2015 (EP) .................................... 15382011

(51) Int. Cl.
*A61K 31/5377* (2006.01)
*C07D 487/04* (2006.01)

(52) U.S. Cl.
CPC ........ *C07D 487/04* (2013.01); *A61K 31/5377* (2013.01)

(58) Field of Classification Search
CPC .......................... A61K 31/5377; C07D 487/04
USPC ........................................ 514/234.2; 544/118
See application file for complete search history.

(56) References Cited

U.S. PATENT DOCUMENTS

2005/0277655 A1 12/2005 Ding et al.

FOREIGN PATENT DOCUMENTS

| WO | WO 2005/121107 A1 | 12/2005 |
| WO | WO 2008/009457 A1 | 1/2008 |
| WO | WO 2008/094602 A2 | 8/2008 |

OTHER PUBLICATIONS

Jorda et al, "Anti-leishmanial activity of disubstituted purines and related pyrazolo[4,3-] pyrimidines", *Bioorganic & Medicinal Chemistry Letters*, vol. 21, No. 14, pp. 4233-4237 (2011).
Alvar et al., "Leishmaniasis Worldwide and Global Estimates of Its Incidence", *PLoS ONE*, vol. 7, Issue 5, e35671, https://doi.org/10.1371/journal.pone.0035671, pp. 1-12 (2012).
Berge et al., "Pharmaceutical Salts", *Journal of Pharmaceutical Sciences*, vol. 66, Issue 1, pp. 1-19 (1977).
Berman et al., "Efficacy and safety of liposomal amphotericin B (AmBisome) for visceral leishmaniasis in endemic developing countries", *Bulletin of the World Health Organization*, vol. 76, No. 1, pp. 25-32 (1998).
Bundgaard, Hans, "Design of Prodrugs", *Elsevier Science Publishers B. V. (Biomedical Division)*, Chapter 1, 97 pages (1985).
Ferres, H., "Pro-drugs of β-lactam antibiotics", *Drugs of Today*, vol. 19, No. 9, pp. 499-538 (1983).
Hailu et al., "Geographical Variation in the Response of Visceral Leishmaniasis to Paromomycin in East Africa: A Multicentre, Open-Label, Randomized Trial", *PLOS Neglected Tropical Diseases*, vol. 4, Issue 10, e709, pp. 1-8 (2010).
Khalil et al., "Safety and Efficacy of Single Dose versus Multiple Doses of AmBisomeH for Treatment of Visceral Leishmaniasis in Eastern Africa: A Randomised Trial", *PLOS Neglected Tropical Diseases*, vol. 8, Issue 1, e2613, pp. 1-9 (2014).
Rycker et al., "Comparison of a High-Throughput High-Content Intracellular Leishmania donovani Assay with an Axenic Amastigote Assay", *Antimicrobial Agents and Chemotherapy*, vol. 57, No. 7, pp. 2913-2922 (2013).
Seifert, Karin, "Structures, Targets and Recent Approaches in Anti-Leishmanial Drug.Discovery and Development", *The Open Medicinal Chemistry Journal*, vol. 5, pp. 31-39 (2011).
Vishnu et al., "Synthesis of functionalized pyrazoles and pyrazolo (3,4-d)pyrimidines as potential leishmanicides", *Indian Journal of Chemistry, Section B, Council of Scientific and Industrial Research (CSIR). IN.*, vol. 34, No. 6, pp. 521-524 (1995).
Zhang et al., "Design, synthesis, and biological evaluation of pyrazolopyrimidine-sulfonamides as potent multiple-mitotic kinase (MMK) inhibitors (part I)", *Bioorganic & Medicinal Chemistry Letters*, vol. 21, pp. 5633-5637 (2011).

*Primary Examiner* — Brenda L Coleman
(74) *Attorney, Agent, or Firm* — Nicole Ginanni; Duke M. Fitch

(57) ABSTRACT

The compound 3,3,3-trifluoro-N-((1,4-trans)-4-((3-((S)-2-methylmorpholino)-IH-pyrazolo[3,4-d]pyrimidin-6-yl)amino)cyclohexyl)propane-1-sulfonamide having the Formula (I) or a salt thereof, its opposite enantiomer, compositions comprising the compound and its use in the treatment or prevention of leishmaniasis, particularly visceral leishmaniasis.

(I)

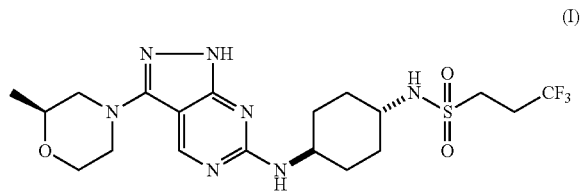

15 Claims, 4 Drawing Sheets

Figure 1. The FT-Raman spectrum of Form 1 of the compound of Formula (I)
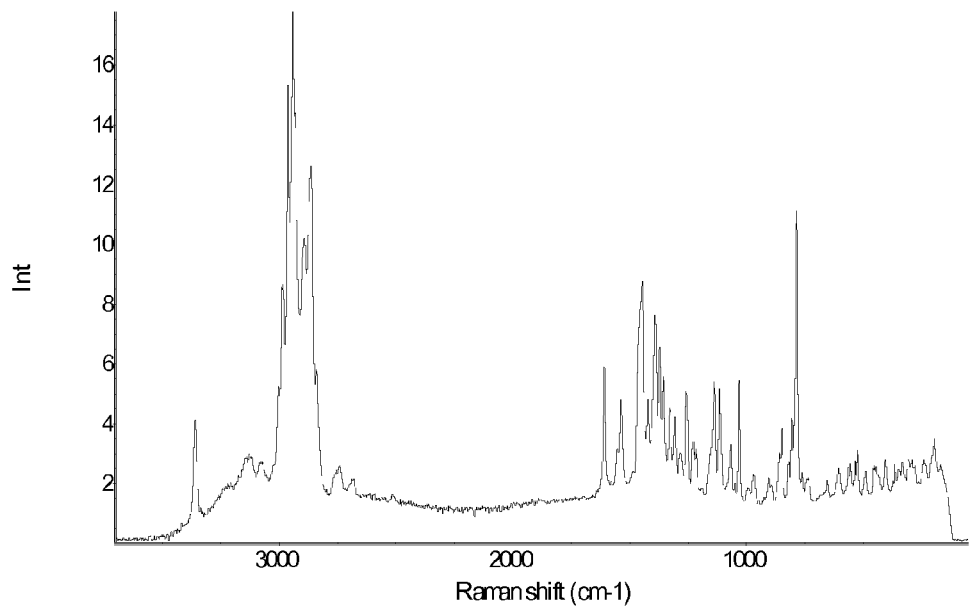
Figure 2. The powder X-ray diffraction (PXRD) pattern of Form 1 of the compound of Formula (I)
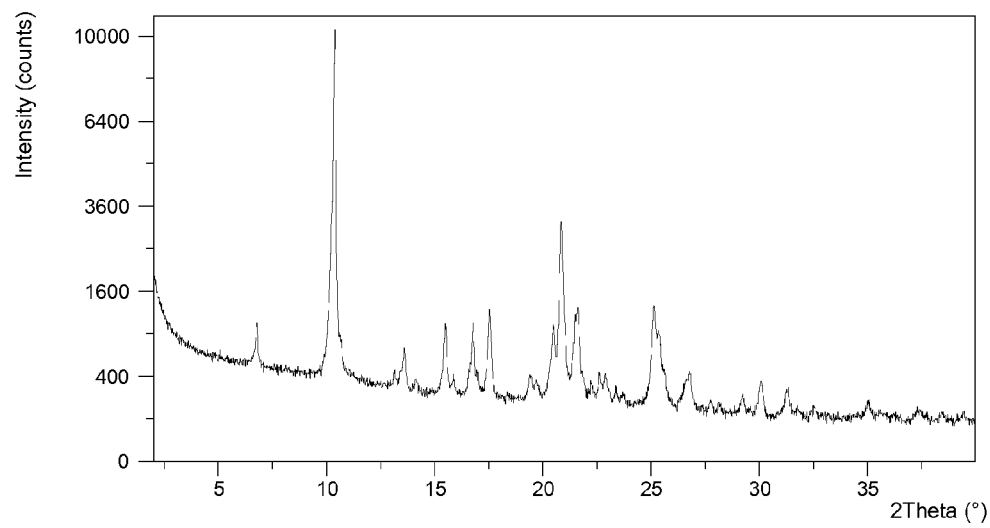

Figure 3. The differential scanning calorimetry (DSC) thermogram for Form 1 of the compound of Formula (I)
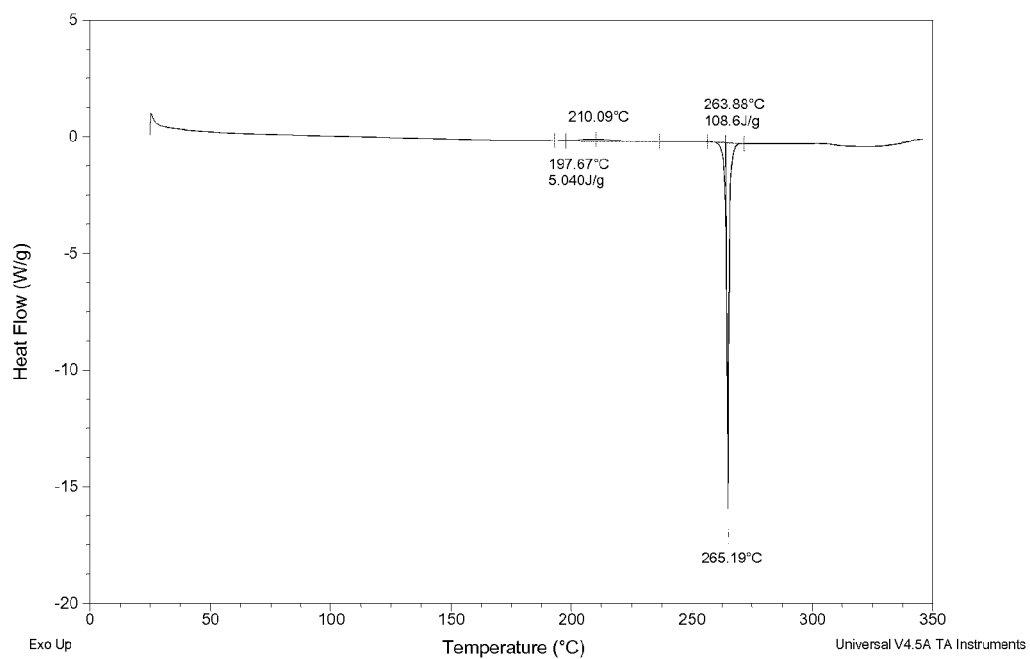
Figure 4. The thermogravimetric analysis (TGA) curve for Form 1 of the compound of Formula (I)
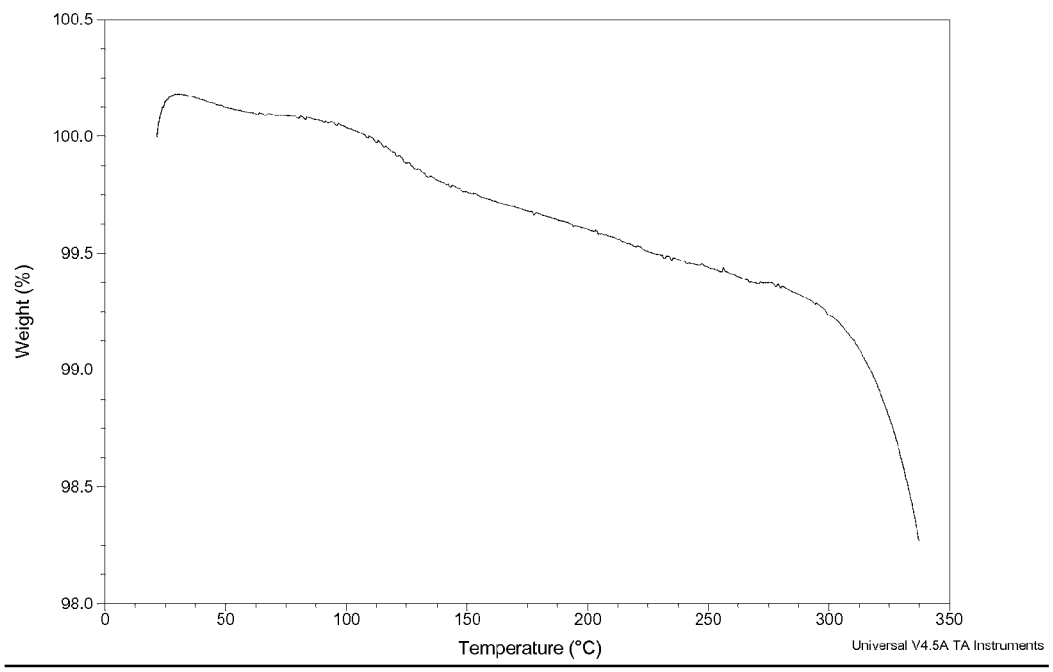

Figure 5. The FT-Raman spectrum of Form 2 of the compound of Formula (I)
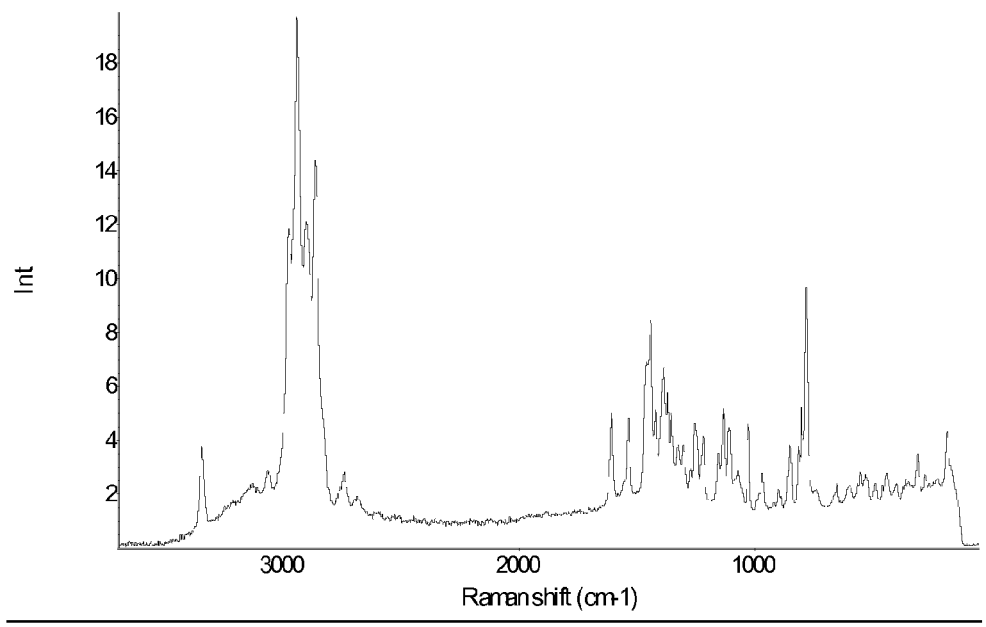
Figure 6. The PXRD pattern of Form 2 of the compound of Formula (I)
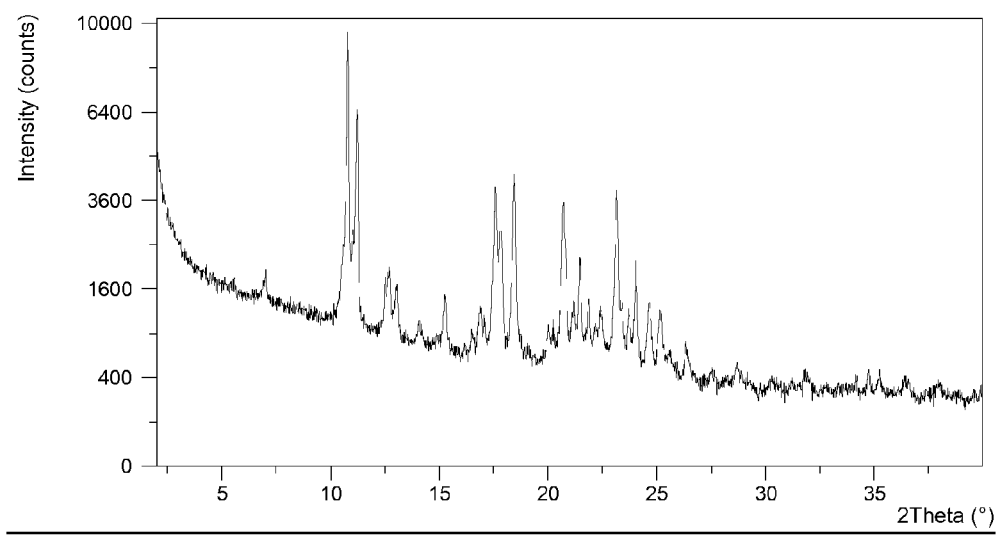

Figure 7. The differential scanning calorimetry (DSC) thermogram for Form 2 of the compound of Formula (I)
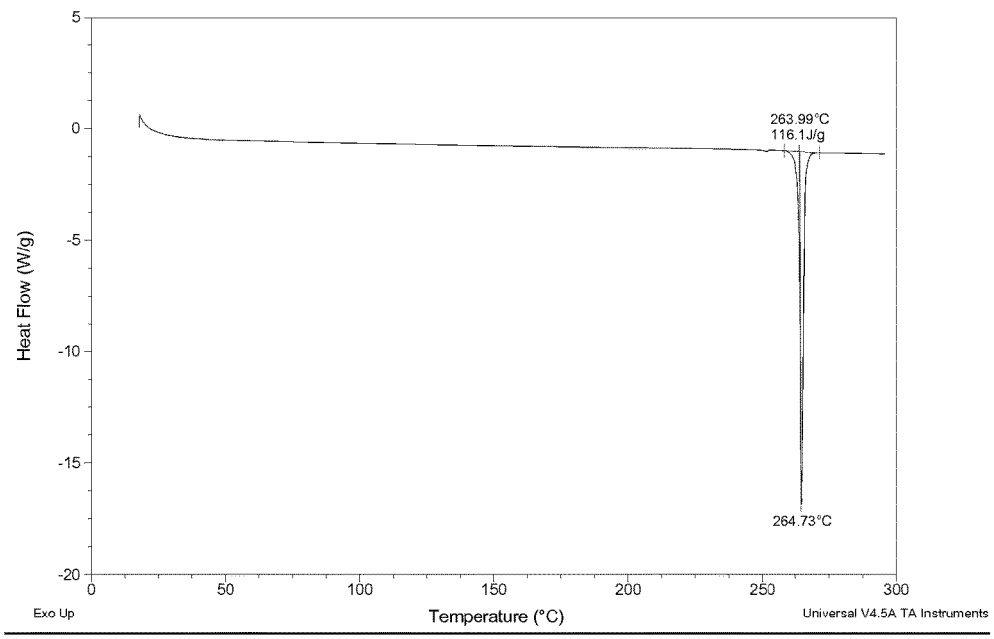
Figure 8. The thermogravimetric analysis (TGA) curve for Form 2 of the compound of Formula (I)
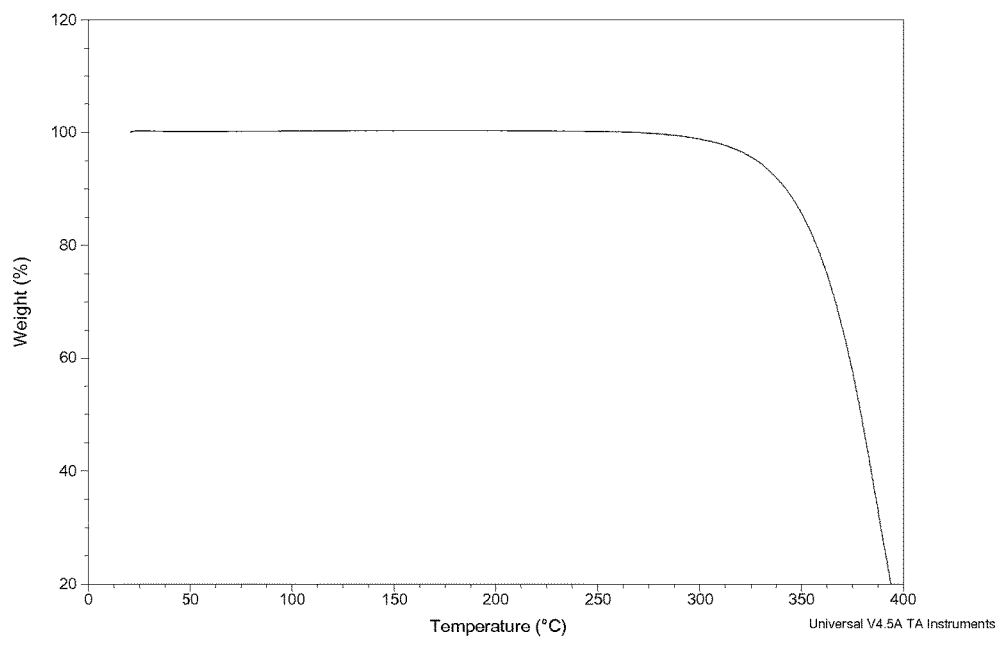

PYRAZOLO[3,4-D]PYRIMIDIN DERIVATIVE AND ITS USE FOR THE TREATMENT OF LEISHMANIASIS

This application is a § 371 application of International Application No. PCT/EP2016/051240, filed Jan. 21, 2016, which claims the benefit of EP 15382011.3, filed Jan. 23, 2015, the disclosures of which are incorporated herein in their entireties.

TECHNICAL FIELD OF THE INVENTION

This invention provides a pyrazolo-pyrimidine compound, its opposite enantiomer, salts thereof, compositions comprising it and its use in therapy, for example in the treatment of the leishmaniasis, particularly visceral leishmaniasis (also known as VL).

BACKGROUND OF THE INVENTION

Leishmaniasis is caused in humans and animals by protozoan parasites from several leishmania species that are transmitted to hosts by the bites of infected female phlebotomine sandflies.

There are three main human forms of leishmaniasis—visceral (often known as kala-azar and the most serious form of the disease), cutaneous (the most common), and mucocutaneous (the most disfiguring). Most leishmaniases are zoonoses (diseases that can be transmitted from animals to humans) and the reservoir hosts include many species of mammals. Dogs are important reservoirs of *L. infantum* responsible for visceral leishmaniasis.

Animals can also suffer from visceral, cutaneous and mucocutaneous forms of the disease.

It is estimated that 350 million people are at risk of the disease (most of them are children), with 1.3 million new cases and 20 000 to 30 000 deaths per year. (Leishmaniasis Worldwide and Global Estimates of Its Incidence. Alvar J. et al. (2012) PLoS ONE 7(5): e35671. doi:10.1371/journal.pone.0035671).

Current treatments have serious drawbacks in terms of efficacy, safety, drug resistance, stability, cost and the majority lack an oral dosing option (Structures, Targets and Recent Approaches in Anti-Leishmanial Drug Discovery and Development. Seifert K., Open Med Chem J. 2011; 5:31-39. doi: 10.2174/1874104501105010031). Geographical efficacy variation in the current treatments has started to be observed—for example, the efficacy of liposomal amphotericin B in East Africa is below what is seen in the Indian sub-continent for the same dosage ((a) Berman J D, Badaro R, Thakur C P, Wasunna K M, Behbehani K, et al. (1998) Efficacy and safety of liposomal amphotericin B (AmBisome) for visceral leishmaniasis in endemic developing countries. Bull World Health Organ 76: 25-32. (b) Eltahir A. G. Khalil, Teklu Weldegebreal, Brima M. Younis et al. Safety and Efficacy of Single Dose versus Multiple Doses of AmBisome® for Treatment of Visceral Leishmaniasis in Eastern Africa: A Randomised Trial. PLOS Neglected Tropical Diseases: published 16 Jan. 2014 (info:doi/10.1371/journal.pntd.0002613). Efficacy rates are also found to vary within Africa (Hailu A, Musa A, Wasunna M, Balasegaram M, Yifru S, et al. (2010) Geographical Variation in the Response of Visceral Leishmaniasis to Paromomycin in East Africa: A Multicentre, Open-Label, Randomized Trial. PLoS Negl Trop Dis 4(10): e709. doi: 10.1371/journal.pntd.0000709).

As such there is a real unmet medical need for new oral drugs and combination therapy for the treatment and potential elimination of this disease in certain geographical areas, requiring the development of multiple new oral agents.

WO 2005/121107 and US 2005/277655 disclose certain pyrazolo-pyrimidine compounds as cyclin-dependent kinase inhibitors useful for the treatment of cancer.

WO 2008/09457, WO 2008/094602 and Bioorganic & Medicinal Chemistry Letters (2011), 21(18), 5633-5637 disclose certain pyrazolo-pyrimidine compounds as protein kinase inhibitors useful for the treatment of cancer.

SUMMARY OF THE INVENTION

The present invention provides the pyrazolo-pyrimidine compound 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide, having the Formula (I):

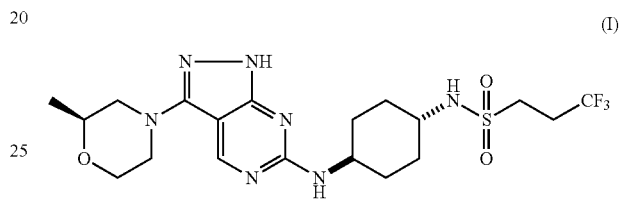

or a salt thereof.

The present invention also provides pharmaceutical compositions comprising the compound of Formula (I), or a pharmaceutically acceptable salt thereof.

Furthermore, the present invention also provides a method of treatment or prevention of leishmaniasis, particularly visceral leishmaniasis, which method comprises administering to a mammal in need thereof, a therapeutically effective amount of a compound of Formula (I), or a pharmaceutically acceptable salt thereof. In one aspect, the mammal is a human.

According to another aspect, the invention provides the compound of Formula (I), or a pharmaceutically acceptable salt thereof, for use in therapy, which therapy is human or veterinary.

In another aspect, the invention provides the compound of Formula (I), or a pharmaceutically acceptable salt thereof, for use in the treatment of leishmaniasis, particularly visceral leishmaniasis.

In another aspect, the invention provides the use of the compound of Formula (I), or a pharmaceutically acceptable salt thereof, in the manufacture of a medicament for the treatment or prevention of leishmaniasis, particularly visceral leishmaniasis.

In a further aspect, the invention provides the opposite enantiomer of a compound of Formula (I) which is 3,3,3-trifluoro-N-((1,4-trans)-4-((3-((R)-2-methylmorpholino)-1H-pyrazolo[3,4-d]pyrimidin-6-yl)amino)cyclohexyl)propane-1-sulfonamide:

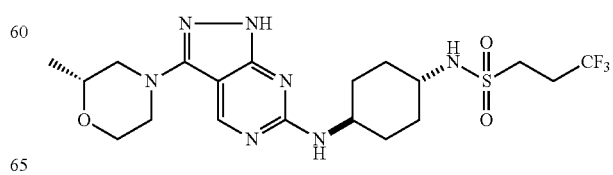

or a salt thereof.

In a yet further aspect, the invention provides a mixture comprising i) a compound of Formula (I) or a salt thereof, and ii) the opposite enantiomer of a compound of Formula (I) which is 3,3,3-trifluoro-N-((1,4-trans)-4-((3-((R)-2-methylmorpholino)-1H-pyrazolo[3,4-d]pyrimidin-6-yl)amino)cyclohexyl)propane-1-sulfonamide or a salt thereof.

DETAILED DESCRIPTION OF THE INVENTION

In a first aspect, the present invention is directed to 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide, the compound of Formula (I):

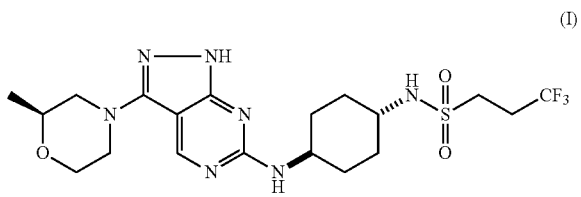

(I)

and salts thereof.

It is to be understood that for the compound of Formula (I), the stereochemistry shown at the positions denoted A and B below is relative stereochemistry, that is to say, the substituents on the cyclohexyl ring at positions A and B have a trans relationship to each other. For the avoidance of doubt, the stereochemistry shown at position C is absolute stereochemistry.

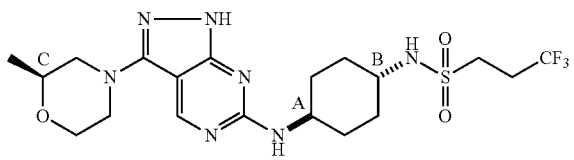

It will be understood by the skilled artisan that the above statements regarding relative and absolute stereochemistry also apply to the opposite enantiomer of the Compound of Formula (I) and also to the prodrugs described hereinbelow. It is also to be understood that the discussion hereinbelow in respect of a compound of Formula (I) is also applicable to its enantiomer, or to a mixture of a compound of Formula (I) and its enantiomer, or a salt of any of these, mutatis mutandis.

It is to be understood that reference herein to "compound(s) of the invention" means a compound of Formula (I), its enantiomer, or a mixture of a compound of Formula (I) and its enantiomer, or a salt of any of these. It is to be further understood that the discussion hereinbelow in respect of a compound of Formula (I) is also applicable to its enantiomer, or to a mixture of a compound of Formula (I) and its enantiomer, or a salt of any of these, mutatis mutandis.

Since a compound of the invention is intended for use in pharmaceutical compositions it will readily be understood that it is provided in substantially pure form, for example at least 60% pure, more suitably at least 75% pure and preferably at least 85%, especially at least 98% pure (% are on a weight for weight basis). Impure preparations of the compound of the invention may be used for preparing the more pure forms used in the pharmaceutical compositions; these less pure preparations of the compounds should contain at least 1%, more suitably at least 5% and preferably from 10 to 59% of a compound of the invention or pharmaceutically acceptable derivative thereof.

In one aspect of the invention, a compound of Formula (I) is in the form of a free base. In a further aspect of the invention, a compound of Formula (I) is in the form of a pharmaceutically acceptable salt.

Salts of the compounds of Formula (I) include pharmaceutically acceptable salts and salts which may not be pharmaceutically acceptable but may be useful in the preparation of compounds of Formula (I) and pharmaceutically acceptable salts thereof. In one aspect of the invention, a compound of Formula (I) is in the form of a pharmaceutically acceptable salt. Salts may be derived from certain inorganic or organic acids or bases.

Examples of salts are pharmaceutically acceptable salts. Pharmaceutically acceptable salts include acid addition salts. For a review on suitable salts see Berge et al., *J. Pharm. Sci.,* 66:1-19 (1977).

Examples of pharmaceutically acceptable acid addition salts of a compound of Formula (I) include inorganic acids such as, for example, hydrochloric acid, hydrobromic acid, orthophosphoric acid, nitric acid, phosphoric acid, or sulfuric acid, or with organic acids such as, for example, methanesulfonic acid, ethanesulfonic acid, p-toluenesulfonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulfonic, naphthalenesulfonic such as 2-naphthalenesuphonic, hexanoic acid or acetylsalicylic acid.

In one aspect of the invention, a compound of Formula (I) is in the form of a hydrochloric acid, hydrobromic acid, orthophosphoric acid, nitric acid, phosphoric acid, or sulfuric acid salt. In another aspect, a compound of Formula (I) is in the form of a hydrochloric acid, maleic acid, p-toluenesulfonic acid or sulfuric acid salt.

Examples of pharmaceutically acceptable inorganic base addition salts of a compound of Formula (I) include salts of ammonium, calcium, copper, ferric, ferrous, lithium, magnesium, manganic, manganous, potassium, sodium, zinc and the like.

The invention includes within its scope all possible stoichiometric and non-stoichiometric forms of the salts of the compounds of Formula (I).

Salts may be formed using techniques well-known in the art, for example by precipitation from solution followed by filtration, or by evaporation of the solvent.

Typically, a pharmaceutically acceptable acid addition salt can be formed by reaction of a compound of Formula (I) with a suitable acid (such as hydrobromic, hydrochloric, sulfuric, maleic, p-toluenesulfonic, methanesulfonic, naphthalenesulfonic or succinic acids), optionally in a suitable solvent such as an organic solvent, to give the salt which is usually isolated for example by crystallisation and filtration.

The compound of Formula (I) may also be prepared as the N-oxide. Examples of the structures of such N-oxides are as follows.

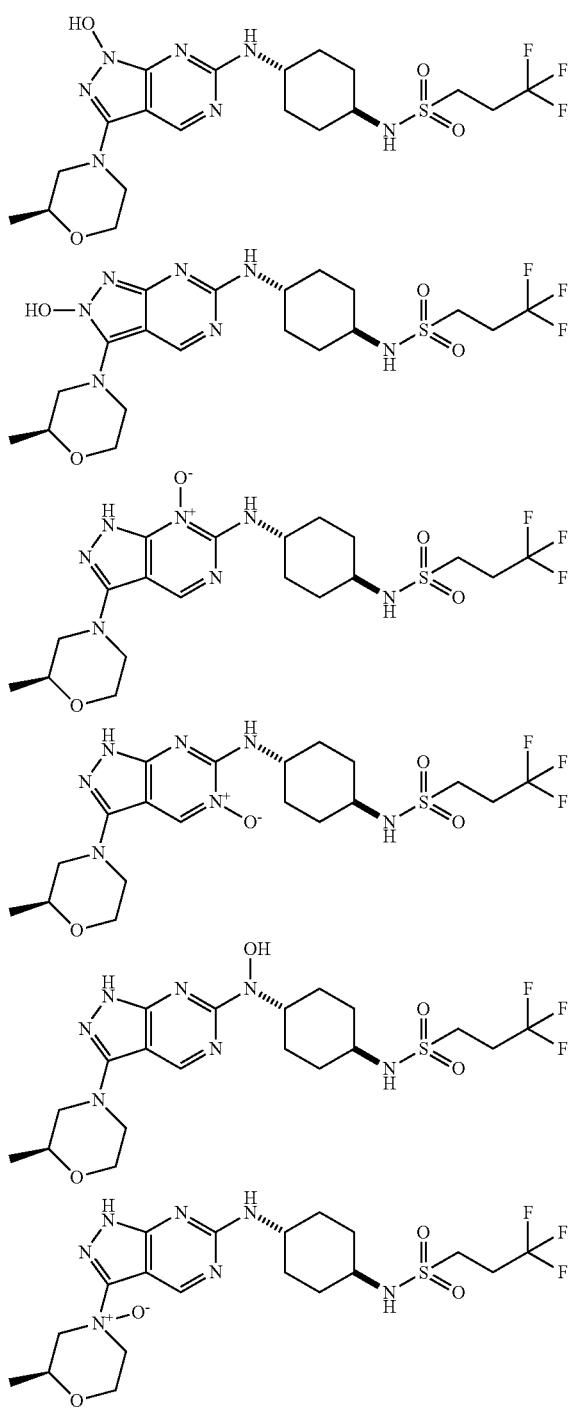

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Accordingly, compounds of Formula (I) may exist as solvates. As used herein, the term solvate encompasses solvates of both a free base compound as well as any salt thereof.

The compounds of the invention contain chiral atoms and hence can exist in one or more stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode. Unless otherwise specified (for example when the absolute stereochemistry is shown), for compounds of the invention which possess at least one stereocentre, and which can therefore form enantiomers, the compound can contain a mixture of enantiomers, for example a 1:1 mixture of enantiomers, i.e. a racemic mixture of enantiomers. This mixture of enantiomers may be separated using conventional techniques such as chiral HPLC. For an isomer of compound of the invention for which the absolute stereochemistry is stated or which is otherwise described as a single enantiomer, said isomer of a compound of the invention has, in one embodiment, at least 80% e.e. In another embodiment, said isomer of a compound of the invention has at least 90% e.e., for example at least 95% e.e. In another embodiment said isomer of compound of the invention corresponds to at least 98% e.e, for example at least 99% e.e.

Accordingly, the invention also provides the opposite enantiomer of a compound of Formula (I) which is, 3,3,3-trifluoro-N-((1,4-trans)-4-((3-((R)-2-methylmorpholino)-1H-pyrazolo[3,4-d]pyrimidin-6-yl)amino)cyclohexyl)propane-1-sulfonamide, or a salt thereof.

The invention also provides a mixture comprising i) a compound of Formula (I) or a salt thereof, and ii) the opposite enantiomer of a compound of Formula (I) which is 3,3,3-trifluoro-N-((1,4-trans)-4-((3-((R)-2-methylmorpholino)-1H-pyrazolo[3,4-d]pyrimidin-6-yl)amino)cyclohexyl)propane-1-sulfonamide or a salt thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest. In one aspect of the invention, the compound of Formula (I) is crystalline.

Polymorphic forms of compounds of the invention may be characterised and differentiated using a number of conventional analytical techniques, including, but not limited to, powder X-ray diffraction (PXRD), infrared spectroscopy (IR), Raman spectroscopy, differential scanning calorimetry (DSC), thermogravimetric analysis (TGA) and solid-state nuclear magnetic resonance (ssNMR).

Fourier Transform Raman Spectroscopy (FT-Raman)

FT-Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. All spectra were acquired at 4 cm$^{-1}$ resolution, 64-128 scans, using Happ-Genzel apodization function and 2-level zero-filling. Band positions were determined using Omnic software and the margin of error in each band position is approximately ±1 cm$^{-1}$.

Powder X-Ray Diffraction (PXRD)

PXRD diffractograms were acquired using PANalytical X'Pert Pro diffractometer on Si zero-background wafers. All diffractograms were collected using a Cu Kα (45 kV/40 mA) radiation and a step size of 0.02° 2θ and X'celerator™ RTMS (Real Time Multi-Strip) detector. Nickel filter was used to reduce unwanted radiation, unless noted otherwise. Configuration on the incidental beam side: fixed divergence slit (¼ deg), 0.04 rad soller slits, anti-scatter slit (¼ deg), and 10 mm beam mask. Configuration on the diffracted beam side: fixed divergence slit (¼ deg) and 0.04 rad soller slit. Peak positions were determined using Highscore software and the margin of error in each peak position expressed in terms of 2 theta angles (2θ) is approximately ±0.1° 2θ.

Differential Scanning Calorimetry (DSC)

DSC was conducted with a TA Instruments Q100 differential scanning calorimeter equipped with an autosampler and a refrigerated cooling system under 40 mL/min $N_2$ purge. DSC thermograms were obtained at 15° C./min in crimped Al pans.

Thermogravimetric Analysis (TGA)

TGA thermograms were obtained with a TA Instruments Q500 thermogravimetric analyzer under 40 mL/min $N_2$ purge at 15° C./min in Pt or Al pans.

Polymorphic Form 1 of the Compound of Formula (I)

In one aspect, the present invention provides a polymorph of the compound of Formula (I) designated "Form 1".

In one aspect, the present invention provides Form 1 of the compound of Formula (I) characterised by substantially the same FT-Raman spectrum as FIG. 1, obtained under the conditions described hereinabove.

In another aspect, the present invention provides Form 1 of the compound of Formula (I) characterised by an FT-Raman spectrum obtained under the conditions described hereinabove and having the following representative peaks:

| Raman band positions for Form 1 Position/cm$^{-1}$ |
| --- |
| 196 ± 1 |
| 240 ± 1 |
| 306 ± 1 |
| 331 ± 1 |
| 364 ± 1 |
| 405 ± 1 |
| 454 ± 1 |
| 489 ± 1 |
| 524 ± 1 |
| 534 ± 1 |
| 554 ± 1 |
| 564 ± 1 |
| 604 ± 1 |
| 653 ± 1 |
| 736 ± 1 |
| 762 ± 1 |
| 785 ± 1 |
| 805 ± 1 |
| 817 ± 1 |
| 849 ± 1 |
| 905 ± 1 |
| 969 ± 1 |
| 1031 ± 1 |
| 1065 ± 1 |
| 1114 ± 1 |
| 1137 ± 1 |
| 1217 ± 1 |
| 1226 ± 1 |
| 1258 ± 1 |
| 1282 ± 1 |
| 1306 ± 1 |
| 1328 ± 1 |
| 1356 ± 1 |
| 1370 ± 1 |
| 1391 ± 1 |
| 1421 ± 1 |
| 1444 ± 1 |
| 1536 ± 1 |
| 1608 ± 1 |
| 2689 ± 1 |
| 2742 ± 1 |
| 2840 ± 1 |
| 2864 ± 1 |
| 2891 ± 1 |
| 2942 ± 1 |
| 2963 ± 1 |
| 2986 ± 1 |
| 3002 ± 1 |
| 3075 ± 1 |
| 3129 ± 1 |
| 3360 ± 1 |

In another aspect, the present invention provides Form 1 of the compound of Formula (I) characterised by an FT-Raman spectrum obtained under the conditions described hereinabove, comprising peaks at 785, 805, 1031, 1114, 1137, 1258, 1306, 1328, 1356, 1370, 1391, 1421, 1444, 1536, 1608, 2864, 2891, 2942, 2963, 2986, and 3360 cm$^{-1}$, wherein the margin of error in each band position is approximately ±1 cm$^{-1}$.

In one aspect, the present invention provides Form 1 of the compound of Formula (I) characterised by substantially the same powder X-ray diffraction (PXRD) pattern as FIG. 2, obtained under the conditions described hereinabove.

In another aspect, the present invention provides Form 1 of the compound of Formula (I) characterised by a powder X-ray diffraction (PXRD) pattern obtained under the conditions described hereinabove and having the following representative peaks:

| PXRD peak positions for Form 1 | |
| --- | --- |
| Position/°2θ | d-spacing [Å] |
| 6.8 ± 0.1 | 13.0 |
| 10.4 ± 0.1 | 8.5 |
| 10.6 ± 0.1 | 8.3 |
| 13.2 ± 0.1 | 6.7 |
| 13.4 ± 0.1 | 6.6 |
| 13.6 ± 0.1 | 6.5 |
| 14.2 ± 0.1 | 6.3 |
| 15.5 ± 0.1 | 5.7 |
| 15.9 ± 0.1 | 5.6 |
| 16.8 ± 0.1 | 5.3 |
| 17.5 ± 0.1 | 5.1 |
| 19.4 ± 0.1 | 4.6 |
| 19.7 ± 0.1 | 4.5 |
| 20.5 ± 0.1 | 4.3 |
| 20.8 ± 0.1 | 4.3 |
| 21.5 ± 0.1 | 4.1 |
| 22.3 ± 0.1 | 4.0 |
| 22.6 ± 0.1 | 3.9 |
| 22.9 ± 0.1 | 3.9 |
| 23.4 ± 0.1 | 3.8 |
| 23.7 ± 0.1 | 3.8 |
| 25.1 ± 0.1 | 3.5 |
| 25.4 ± 0.1 | 3.5 |
| 26.8 ± 0.1 | 3.3 |
| 27.8 ± 0.1 | 3.2 |
| 29.2 ± 0.1 | 3.1 |
| 29.8 ± 0.1 | 3.0 |
| 30.1 ± 0.1 | 3.0 |
| 31.3 ± 0.1 | 2.9 |

-continued

| PXRD peak positions for Form 1 | |
|---|---|
| Position/°2θ | d-spacing [Å] |
| 32.5 ± 0.1 | 2.8 |
| 35.1 ± 0.1 | 2.6 |
| 37.4 ± 0.1 | 2.4 |

In a further aspect, the present invention provides Form 1 of the compound of Formula (I) characterised by a powder X-ray diffraction (PXRD) pattern obtained under the conditions described hereinabove, comprising 2 theta (2θ) angles at 6.8, 10.4, 15.5, 16.8, 17.5, 20.5, 20.8, 21.5 and 23.7 degrees, the margin of error in each peak position being approximately ±0.1° 2θ.

In one aspect, the present invention provides Form 1 of the compound of Formula (I) characterised by substantially the same differential scanning calorimetry (DSC) thermogram as FIG. 3, obtained under the conditions described hereinabove.

In one aspect, the present invention provides Form 1 of the compound of Formula (I) characterised by substantially the same thermogravimetric analysis (TGA) curve as FIG. 4, obtained under the conditions described hereinabove.

Polymorphic Form 2 of the Compound of Formula (I)

In one aspect, the present invention provides a polymorph of the compound of Formula (I) designated "Form 2".

In one aspect, the present invention provides Form 2 of the compound of Formula (I) characterised by substantially the same FT-Raman spectrum as FIG. 5, obtained under the conditions described hereinabove.

In another aspect, the present invention provides Form 2 of the compound of Formula (I) characterised by an FT-Raman spectrum obtained under the conditions described hereinabove and having the following representative peaks:

| Raman band positions for Form 2 Position/cm$^{-1}$ |
|---|
| 185 ± 1 |
| 279 ± 1 |
| 310 ± 1 |
| 400 ± 1 |
| 440 ± 1 |
| 489 ± 1 |
| 530 ± 1 |
| 553 ± 1 |
| 599 ± 1 |
| 652 ± 1 |
| 784 ± 1 |
| 803 ± 1 |
| 814 ± 1 |
| 851 ± 1 |
| 900 ± 1 |
| 970 ± 1 |
| 1029 ± 1 |
| 1074 ± 1 |
| 1108 ± 1 |
| 1133 ± 1 |
| 1156 ± 1 |
| 1219 ± 1 |
| 1257 ± 1 |
| 1274 ± 1 |
| 1304 ± 1 |
| 1326 ± 1 |
| 1357 ± 1 |
| 1371 ± 1 |
| 1388 ± 1 |
| 1423 ± 1 |
| 1443 ± 1 |
| 1537 ± 1 |
| 1609 ± 1 |
| 2744 ± 1 |
| 2867 ± 1 |
| 2905 ± 1 |
| 2945 ± 1 |
| 2980 ± 1 |
| 3069 ± 1 |
| 3133 ± 1 |
| 3349 ± 1 |

In another aspect, the present invention provides Form 2 of the compound of Formula (I) characterised by an FT-Raman spectrum obtained under the conditions described hereinabove, comprising peaks at 784, 804, 851, 1029, 1108, 1133, 1219, 1257, 1304, 1357, 1371, 1388, 1423, 1443, 1537, 1609, 2867, 2905, 2945, 2980, and 3349 cm$^{-1}$, wherein the margin of error in each band position is approximately ±1 cm$^{-1}$.

In one aspect, the present invention provides Form 2 of the compound of Formula (I) characterised by substantially the same powder X-ray diffraction (PXRD) pattern as FIG. 6, obtained under the conditions described hereinabove.

In another aspect, the present invention provides Form 2 of the compound of Formula (I) characterised by a powder X-ray diffraction (PXRD) pattern obtained under the conditions described hereinabove and having the following representative peaks:

| PXRD peak positions for Form 2 | |
|---|---|
| Position/°2θ | d-spacing [Å] |
| 7.0 ± 0.1 | 12.6 |
| 10.8 ± 0.1 | 8.2 |
| 11.2 ± 0.1 | 7.9 |
| 12.5 ± 0.1 | 7.1 |
| 12.7 ± 0.1 | 7.0 |
| 13.1 ± 0.1 | 6.8 |
| 14.1 ± 0.1 | 6.3 |
| 15.3 ± 0.1 | 5.8 |
| 16.9 ± 0.1 | 5.2 |
| 17.6 ± 0.1 | 5.0 |
| 17.8 ± 0.1 | 5.0 |
| 18.4 ± 0.1 | 4.8 |
| 20.0 ± 0.1 | 4.4 |
| 20.2 ± 0.1 | 4.4 |
| 20.7 ± 0.1 | 4.3 |
| 21.2 ± 0.1 | 4.2 |
| 21.5 ± 0.1 | 4.1 |
| 21.9 ± 0.1 | 4.1 |
| 22.4 ± 0.1 | 4.0 |
| 23.2 ± 0.1 | 3.8 |
| 23.7 ± 0.1 | 3.8 |
| 24.0 ± 0.1 | 3.7 |
| 24.6 ± 0.1 | 3.6 |
| 25.2 ± 0.1 | 3.5 |
| 26.4 ± 0.1 | 3.4 |
| 27.5 ± 0.1 | 3.2 |
| 28.7 ± 0.1 | 3.1 |
| 30.4 ± 0.1 | 2.9 |
| 31.9 ± 0.1 | 2.8 |
| 34.7 ± 0.1 | 2.6 |
| 35.2 ± 0.1 | 2.5 |
| 36.5 ± 0.1 | 2.5 |
| 38.0 ± 0.1 | 2.4 |

In a further aspect, the present invention provides Form 2 of the compound of

Formula (I) characterised by a powder X-ray diffraction (PXRD) pattern obtained under the conditions described hereinabove, comprising 2 theta (2θ) angles at 7.0, 10.8, 11.2, 12.7, 13.1, 15.3, 17.6, 17.8, 18.4, 20.7, 21.5, 23.2 and 24.0 degrees, the margin of error in each peak position being approximately ±0.1° 2θ.

In one aspect, the present invention provides Form 2 of the compound of Formula (I) characterised by substantially the same differential scanning calorimetry (DSC) thermogram as FIG. 7, obtained under the conditions described hereinabove.

In one aspect, the present invention provides Form 2 of the compound of Formula (I) characterised by substantially the same thermogravimetric analysis (TGA) curve as FIG. 8, obtained under the conditions described hereinabove.

BRIEF DESCRIPTION OF THE DRAWINGS

FIG. 1. The FT-Raman spectrum of Form 1 of the compound of Formula (I), obtained under the conditions described hereinabove. The x-axis is wavenumber in $cm^{-1}$ and the y-axis is intensity in arbitrary units.

FIG. 2. The powder X-ray diffraction (PXRD) pattern of Form 1 of the compound of Formula (I), obtained under the conditions described hereinabove. The x axis is in 2 theta angles and the y axis is intensity in arbitrary units.

FIG. 3. The differential scanning calorimetry (DSC) thermogram for Form 1 of the compound of Formula (I), obtained under the conditions described hereinabove. The DSC heating curve shows an exotherm with an onset temperature of 197.67° C. followed by a melt endotherm with an onset temperature of 263.88° C.

FIG. 4. The thermogravimetric analysis (TGA) curve for Form 1 of the compound of Formula (I), obtained under the conditions described hereinabove. The TGA heating curve shows negligible weight loss until approximately 300° C.

FIG. 5. The FT-Raman spectrum of Form 2 of the compound of Formula (I), obtained under the conditions described hereinabove. The x-axis is wavenumber in $cm^{-1}$ and the y-axis is intensity in arbitrary units.

FIG. 6. The PXRD pattern of Form 2 of the compound of Formula (I), obtained under the conditions described hereinabove. The x axis is in 2 theta angles and the y axis is intensity in arbitrary units.

FIG. 7. The differential scanning calorimetry (DSC) thermogram for Form 2 of the compound of Formula (I), obtained under the conditions described hereinabove. The DSC heating curve shows a single melt endotherm with an onset temperature of 263.99° C.

FIG. 8. The thermogravimetric analysis (TGA) curve for Form 2 of the compound of Formula (I), obtained under the conditions described hereinabove. The TGA heating curve shows negligible weight loss until approximately 300° C.

The compounds of the invention may also be prepared as an amorphous molecular dispersion of drug substance in a polymer matrix such as HPMCAS (hydroxypropylmethylcellulose acetate succinate) using a process such as spray-dried dispersion (SDD). Such a technique is employed to improve properties such as stability and solubility.

Compounds of Formula (I) may exist in the form of isotopic variations. An isotopic variation of a compound of Formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of a compound of Formula (I) or a salt or solvate thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of a compound of Formula (I), or a pharmaceutically salt thereof, can generally be prepared by conventional procedures such as by the illustrative methods or by the preparations described in the Examples hereafter using appropriate isotopic variations of suitable reagents.

It will be appreciated from the foregoing, that compounds of Formula (I) and salts thereof may exist as solvates, or hydrates.

It will be appreciated by those skilled in the art that certain derivatives of the compounds of Formula (I), whilst not necessarily possessing pharmacological activity as such, may be administered and thereafter metabolised in the body to form compounds of Formula (I) which compounds are pharmacologically active. Such derivatives are herein referred to as "prodrugs" and are included within the scope of the invention. Examples of suitable derivatives are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1. Examples of prodrugs of compounds of Formula (I) are shown in Formula (II):

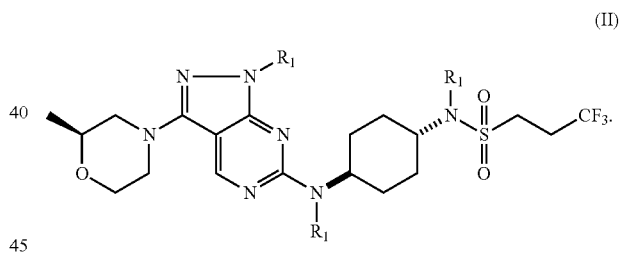

(II)

Wherein

Each $R_1$ is independently selected from H, $C(O)OL_1R_2$, $CL_1R_3OL_1R_2$, $C(O)L_1R_2$ or $P(O)(OL_1R_2)(OL_1R_3)$;

Each $L_1$ is independently selected from a bond or X;

X is $C_{1-6}$alkylene, $C_{1-6}$haloalkylene, $C_{4-6}$heterocyclylene, phenylene or $C_{5-6}$heteroarylene, each of which is optionally substituted by 1 to 4 substituents independently selected from Z;

Z is H, halo, $C(O)L_1R_2$, $C(O)OL_1R_2$, $C(O)NHL_1R_2$, $C(O)N(L_1R_2)(L_1R_3)$, $NH_2$, $OL_1R_2$, $NH(L_1R_2)$, $N(L_1R_2)(L_1R_3)$, or $P(O)(OL_1R_2)(OL_1R_3)$;

Either a) Each $R_2$ and $R_3$ is independently selected from H or Y;

Y is $C_{1-6}$alkyl, $C_{1-6}$haloalkyl, $C_{4-6}$heterocyclyl, phenyl or $C_{5-6}$heteroaryl, each of which is optionally substituted by 1 to 4 substituents independently selected from Z;

Or b) $R_2$ and $R_3$ are bound together to form a linker group $L_1$, so as to form together with the atoms to which they are attached a $C_{4-6}$cycloalkyl or, $C_{4-6}$heterocyclyl group.

Further examples of prodrugs of compounds of Formula (I) are shown in compounds of Formula (III) or (IV), or a pharmaceutically acceptable salt thereof:

(III)

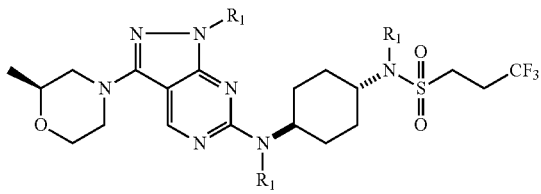

or (IV)

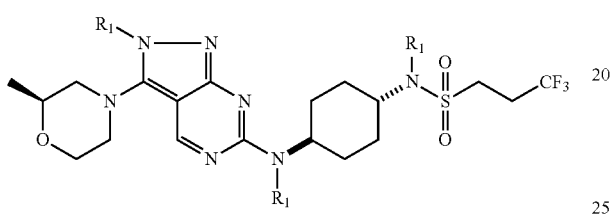

Wherein

Each $R_1$ is independently selected from H, $C(O)OL_1R_2$, $CH(L_1R_3)OL_1R_2$, $CH_2OL_1R_2$, $C(L_1R_3)(L_1R_4)OL_1R_2$, $C(O)OL_1R_2$, $C(O)C(L_1R_2)=C(L_1R_3)L_1R_4P(O)(OL_1R_2)(OL_1R_3)$, $C(O)OL_1OP(O)(OL_1R_2)(OL_1R_3)$, or $C(O)OL_1OC(O)L_1-L_1OP(O)(OL_1R_2)(OL_1R_3)$;

Each $L_1$ is independently selected from a bond or X;

X is $C_{1-6}$alkylene, $C_{2-6}$alkenylene, $C_{2-6}$alkynylene, $C_{4-7}$cycloalkylene, $C_{5-7}$cycloalkenylene, $C_{4-7}$heterocycloalkylene, $C_5$-$C_7$heterocycloalkenylene, phenylene or $C_{5-6}$heteroarylene; each of which is optionally substituted by 1 to 6 substituents independently selected from Z;

Each Z is independently selected from halo, $C(O)L_1R_2$, $C(O)OL_1R_2$, $C(O)NHL_1R_2$, $C(O)N(L_1R_2)(L_1R_3)$, $OL_1R_2$, $N(L_1R_2)(L_1R_3)$, CN, $S(L_1R_2)$, $S(O)(L_1R_2)$, $SO_2(L_1R_2)$ or $P(O)(OL_1R_2)(OL_1R_3)$;

Either a) Each $R_2$, $R_3$ and $R_4$ is independently selected from H or Y;

or b) Each $R_2$, $R_3$ and $R_4$ is independently selected from Y, wherein two of said $R_2$, $R_3$ and $R_4$ are bound together through an additional $L_1$ group so as to form a cyclic group;

Y is Z or $C_{1-6}$alkyl, $C_{1-6}$alkenyl, $C_{2-6}$alkynyl, $C_{4-7}$cycloalkyl, $C_{5-7}$cycloalkenyl, $C_{4-7}$heterocycloalkyl, $C_5$-$C_7$heterocycloalkenyl, phenyl or $C_{5-6}$heteroaryl, each of which is optionally substituted by 6 substituents independently selected from Z.

In one embodiment of Formula (III) or of Formula (IV), each $R_1$ is independently selected from H, $C(O)OL_1R_2$, $CH(L_1R_3)OL_1R_2$, $CH_2OL_1R_2$, $C(L_1R_3)(L_1R_4)OL_1R_2$, $C(O)L_1R_2$, $P(O)(OL_1R_2)(OL_1R_3)$, $C(O)OL_1OP(O)(OL_1R_2)(OL_1R_3)$, or $C(O)OL_1OC(O)L_1-L_1OP(O)(OL_1R_2)(OL_1R_3)$.

Examples of prodrugs of compounds of Formula (I) are as follows, wherein each R is independently selected from H, fluoro or methyl:

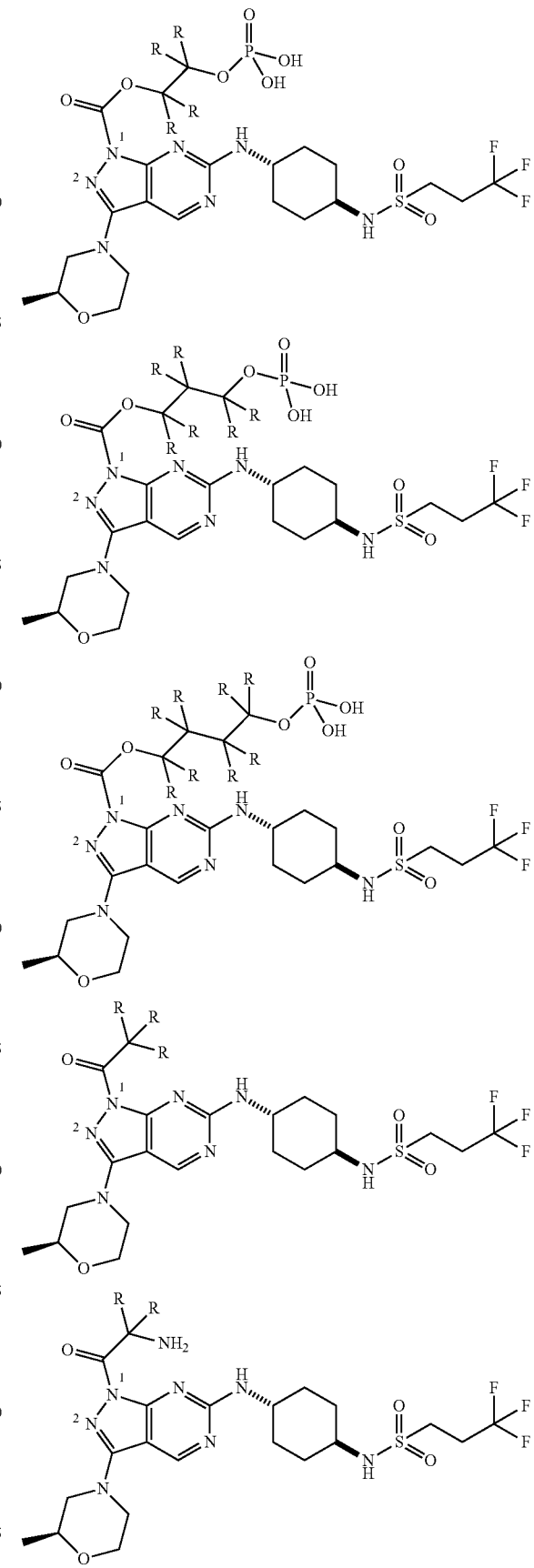

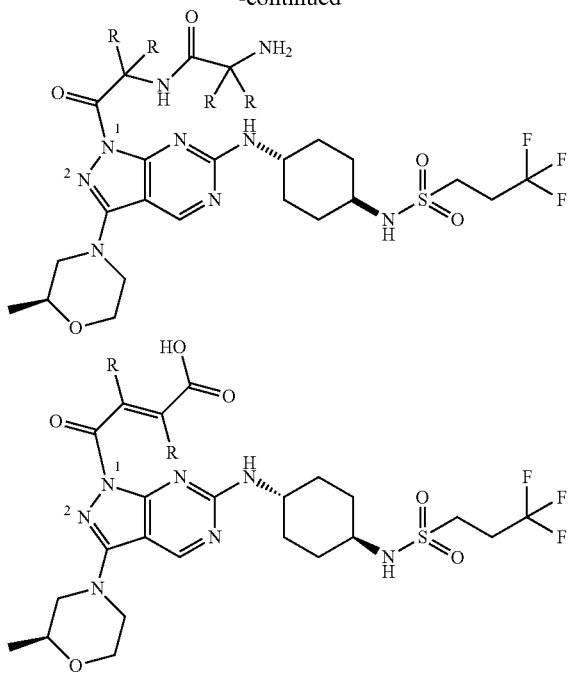

It should be noted that for each of the above Examples, the substituent shown at the nitrogen atom labelled "1" may alternatively be attached to the nitrogen atom labelled "2".

As used herein for Formula (II), the term "$C_{1-6}$alkyl" means a straight or branched alkyl containing at least one, and at most six, carbon atoms. Examples of $C_{1-6}$alkyl include, but are not limited to, methyl, ethyl, propyl, isopropyl, n-butyl, isobutyl, tert-butyl, pentyl, neopentyl, or hexyls.

As used herein for Formula (II), the term "$C_{1-6}$haloalkyl" means $C_{1-6}$alkyl wherein one or more of the hydrogen atoms are replaced with halo.

As used herein for Formula (II), the term "$C_{1-6}$alkylene" means a divalent radical of $C_{1-6}$alkyl. Examples of $C_{1-6}$alkylene include, but are not limited to, methylene, ethylene, isopropylene, n-butylene, isobutylene, tert-butylene, pentylene, neopentylene, or hexylenes.

As used herein for Formula (II), the term "$C_{1-6}$haloalkylene" means a means a divalent radical of $C_{1-6}$haloalkyl as defined herein.

As used herein for Formula (II), the term "$C_{4-6}$cycloalkyl" means a non-aromatic carbocyclic ring containing at least four and at most six carbon atoms. Examples of $C_{4-6}$cycloalkyl groups include cyclobutyl, cyclopentyl and cyclohexyl.

As used herein for Formula (II), the term "$C_{4-6}$heterocyclyl" means a saturated ring containing at least four and at most six atoms, which includes one or more (e.g. 2) ring heteroatoms selected from nitrogen, oxygen and sulfur. Examples of $C_{4-6}$heterocyclyl groups include, but are not limited to, tetrahydropyranyl, tetrahydrofuranyl, tetrahydrothiophenyl, piperidinyl, piperazinyl, morpholinyl, 1,4-dioxanyl, thiomorpholinyl, 1,4-oxathianyl and 1,4-dithanyl. The point of attachment to the rest of the molecule may be by any suitable carbon or nitrogen atom.

As used herein for Formula (II), the term "$C_{4-6}$heterocyclylene" means a divalent radical of a $C_{4-6}$heterocyclyl group as defined herein.

As used herein for Formula (II), the term "$C_{5-6}$heteroaryl" refers to an optionally substituted aromatic ring comprising five or six heteroatoms selected from N, O and S. Examples of $C_{5-6}$heteroaryl groups include, but are not limited to, furanyl, thiophenyl, pyrrolyl, pyridyl, pyrimidyl, imidazolyl and isoxazolyl. Optional heteroaryl substituents include halo, and alkyl.

As used herein for Formula (II), the term "$C_{5-6}$heteroarylene" means a divalent radical of $C_{5-6}$heteroaryl as defined herein.

As used herein for Formula (II), the term "phenylene" means a means a divalent radical of phenyl.

As used herein for Formula (II), the term "halo" refers to fluoro, chloro, bromo or iodo.

As used herein for Formula (III) or Formula (IV), the term "$C_{1-6}$alkyl" means a straight or branched saturated hydrocarbon group containing at least one, and at most six, carbon atoms. Examples of $C_{1-6}$alkyl include, but are not limited to, methyl, ethyl, n-propyl, isopropyl, n-butyl, isobutyl, tert-butyl, pentyl, neopentyl, or hexyls.

As used herein for Formula (III) or Formula (IV), the term "$C_{1-6}$alkylene" means a divalent radical of $C_{1-6}$alkyl as defined herein. Examples of $C_{1-6}$alkylene include, but are not limited to, methylene, ethylene, n-propylene, isopropylene, n-butylene, isobutylene, tert-butylene, pentylene, neopentylene, or hexylenes.

As used herein for Formula (III) or Formula (IV), the term "$C_{2-6}$alkenyl" means a straight or branched unsaturated hydrocarbon group containing at least two, and at most six, carbon atoms, wherein the hydrocarbon group has one or more positions of unsaturation each of which is present as a double bond. Examples of $C_2$-$C_6$alkenyl include, but are not limited to, ethenyl (—CH=CH—), propenyl (—CH$_2$—CH=CH—), isopropenyl, butenyl, pentenyl, hexenyl, 1-propenyl, 2-butenyl and 2-methyl-2-butenyl.

As used herein for Formula (III) or Formula (IV), the term "$C_{2-6}$alkenylene" means a divalent radical of $C_{2-6}$alkenyl as defined herein. Examples of $C_2$-$C_6$alkenylene include, but are not limited to, ethenylene, n-propenylene, isopropenylene, n-butenylene, isobutenylene, tert-butenylene, pentenylene, neopentenylene, or hexenylenes.

As used herein for Formula (III) or Formula (IV), the term "$C_{2-6}$alkynyl" means a straight or branched unsaturated hydrocarbon group containing at least two, and at most six, carbon atoms, wherein the hydrocarbon group has one or more positions of unsaturation each of which is present as a triple bond. Examples of $C_2$-$C_6$alkynyl include, but are not limited to, ethynyl (—CH=CH—), propynyl (—CH$_2$—CH=CH—), butynyl, pentynyl, hexynyl, 1-propynyl, 2-butynyl and 2-methyl-2-butynyl.

As used herein for Formula (III) or Formula (IV), the term "$C_{2-6}$alkynylene" means a divalent radical of $C_{2-6}$alkynyl as defined herein. Examples of $C_2$-$C_6$alkenylene include, but are not limited to, ethynylene, n-propynylene, n-butynylene, isobutynylene, tert-butynylene, pentynylene, neopentynylene, or hexynylenes.

As used herein for Formula (III) or Formula (IV), the term "$C_{4-7}$cycloalkyl" means a non-aromatic carbocyclic saturated ring containing at least four and at most seven carbon atoms. Examples of $C_{4-7}$cycloalkyl groups include, but are not limited to, cyclobutyl, cyclopentyl, cyclohexyl and cycloheptyl.

As used herein for Formula (III) or Formula (IV), the term "$C_{4-7}$cycloalkylene" means a divalent radical of $C_{4-7}$cycloalkyl as defined herein.

As used herein for Formula (III) or Formula (IV), the term "$C_{5-7}$cycloalkenyl" means a non-aromatic carbocyclic unsaturated ring containing at least five and at most seven carbon atoms. Examples of $C_{5-7}$cycloalkenyl groups include, but are not limited to, cyclopentenyl, cyclohexenyl and cycloheptenyl.

As used herein for Formula (III) or Formula (IV), the term "$C_{5-7}$cycloalkenylene" means a divalent radical of $C_{5-7}$cycloalkenyl as defined herein.

As used herein for Formula (III) or Formula (IV), the term "$C_{4-7}$heterocycloalkyl" means a saturated ring containing at least four and at most seven atoms, which includes at least one heteroatom in the ring selected from nitrogen, oxygen and sulfur. Examples of $C_{4-7}$heterocycloalkyl groups include, but are not limited to, tetrahydropyranyl, tetrahydrofuranyl, tetrahydrothiophenyl, tetrahydrothiopyranyl, pyrrolidinyl, piperidinyl, piperazinyl, morpholinyl, 1,4-dioxanyl, thiomorpholinyl, 1,4-oxathianyl, 1,4-dithanyl, dioxepanyl, azepanyl, oxepanyl and diazepanyl. The point of attachment to the rest of the molecule may be by any suitable carbon or nitrogen atom.

As used herein for Formula (III) or Formula (IV), the term "$C_{4-7}$heterocycloalkylene" means a divalent radical of a $C_{4-7}$heterocycloalkyl group as defined herein.

As used herein for Formula (III) or Formula (IV), the term "$C_5$-$C_7$heterocycloalkenyl" means a non-aromatic unsaturated ring containing at least five and at most seven atoms, which includes at least one heteroatom in the ring selected from nitrogen, oxygen and sulfur. Examples of $C_5$-$C_7$heterocycloalkenyl groups include, but are not limited to, dihydropyranyl, dihydrofuranyl, dihydrothiophenyl, pyrrolinyl, azepinyl, oxepinyl, thiepiny, dioxepinyl, dihydropyrrolyl, dihydropyrazolyl, dihydroimidazolyl, dihydrooxazolyl, dihydrothiazolyl and dihydrothiopyranyl.

As used herein for Formula (III) or Formula (IV), the term "$C_5$-$C_7$heterocycloalkenylene" means a divalent radical of $C_5$-$C_7$heterocycloalkenyl as defined herein.

As used herein for Formula (III) or Formula (IV), the term "$C_{5-6}$heteroaryl" refers to an aromatic ring containing at least five and at most six atoms, and comprising at least one heteroatom in the ring selected from nitrogen, oxygen and sulfur. Examples of $C_{5-6}$heteroaryl groups include, but are not limited to, furanyl, thiophenyl, pyrrolyl, pyridyl, pyrimidyl, imidazolyl and isoxazolyl. The point of attachment to the rest of the molecule may be by any suitable carbon or nitrogen atom.

As used herein for Formula (III) or Formula (IV), the term "$C_{5-6}$heteroarylene" means a divalent radical of $C_{5-6}$heteroaryl as defined herein.

As used herein for Formula (III) or Formula (IV), the term "phenylene" means a means a divalent radical of phenyl.

As used herein for Formula (III) or Formula (IV), the term "halo" refers to fluoro, chloro, bromo or iodo.

Accordingly, in one aspect of the invention there is provided a compound of Formula (II), (III) or (IV), or a pharmaceutically acceptable salt thereof. In another aspect there is provided a compound of Formula (III) or (IV), or a pharmaceutically acceptable salt thereof. In a further aspect there is provided a compound of Formula (III). In another aspect there is provided a compound of Formula(IV).

In another aspect of the invention there is provided a pharmaceutical composition comprising a compound of Formula (III) or (IV), or a pharmaceutically acceptable salt thereof, together with at least one pharmaceutically acceptable carrier.

In a further aspect there is provided a combination comprising (a) a compound of Formula (III) or (IV), or a pharmaceutically acceptable salt thereof, and (b) at least one additional therapeutic agent.

In another aspect there is provided a compound of Formula (III) or (IV), or a pharmaceutically acceptable salt thereof, for use in therapy.

In yet another aspect there is provided a compound of Formula (III) or (IV), or a pharmaceutically acceptable salt thereof, for use in the treatment or prevention of leishmaniasis.

In a further aspect, there is provided the use of a compound of Formula (III) or (IV), or a pharmaceutically acceptable salt thereof, in the manufacture of a medicament for the treatment or prevention of leishmaniasis.

In another aspect, there is provided a method of treatment or prevention of leishmaniasis, which method comprises administering to a mammal in need thereof, a therapeutically effective amount of a compound a compound of Formula (III) or (IV), or a pharmaceutically acceptable salt thereof.

Compound Preparation

The compound of Formula (I) and salts thereof, may be prepared by the methodology described hereinafter, constituting further aspects of this invention.

The general procedures which can be used to synthesise the compound of Formula (I) are summarised in reaction Schemes 1, 2 and 3 are illustrated in the Examples.

Scheme 1

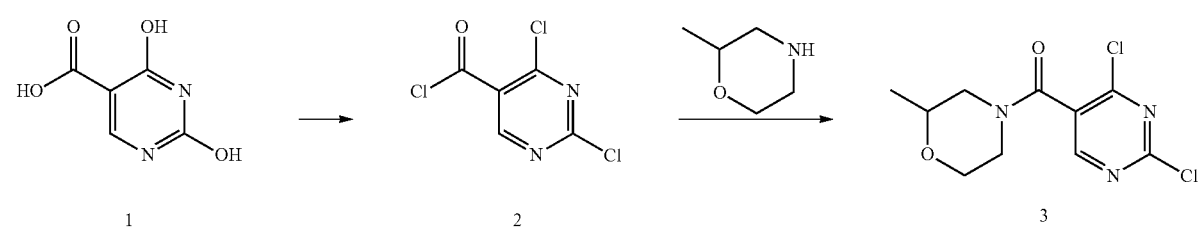

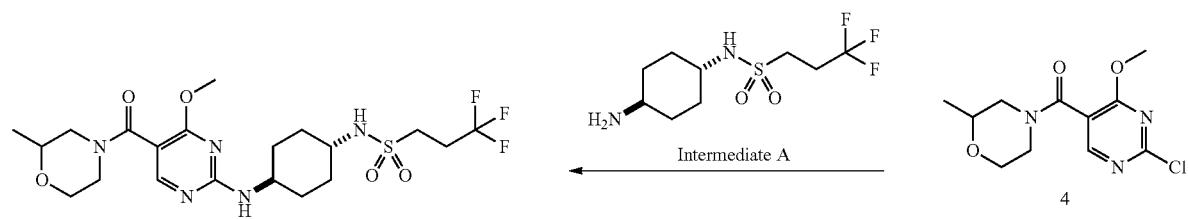
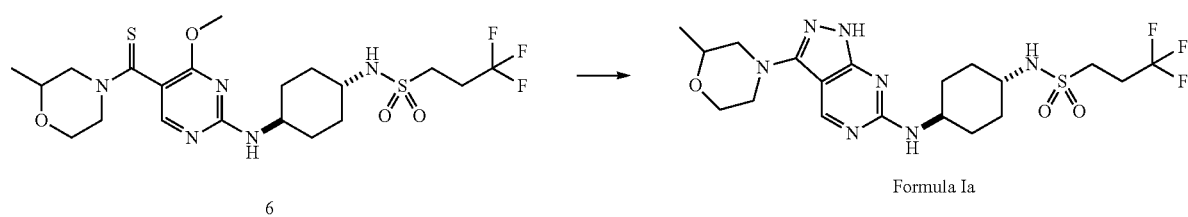
Formula Ia
Chiral separation
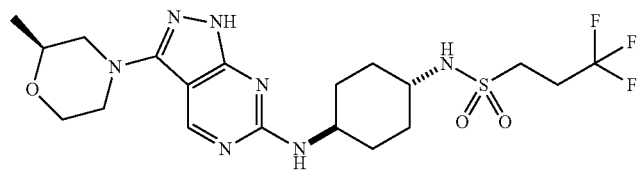
Formula I
Scheme 2
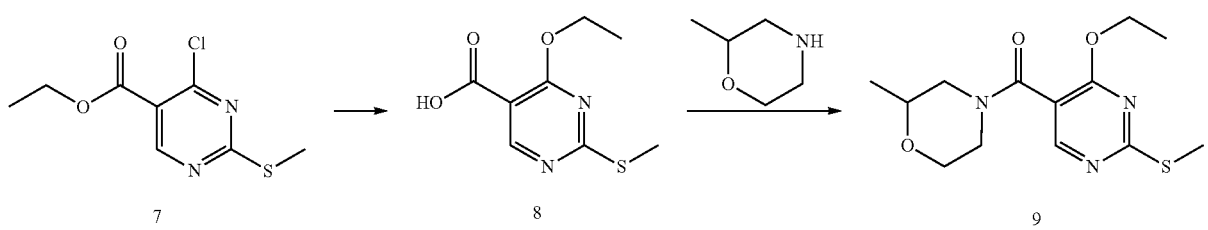

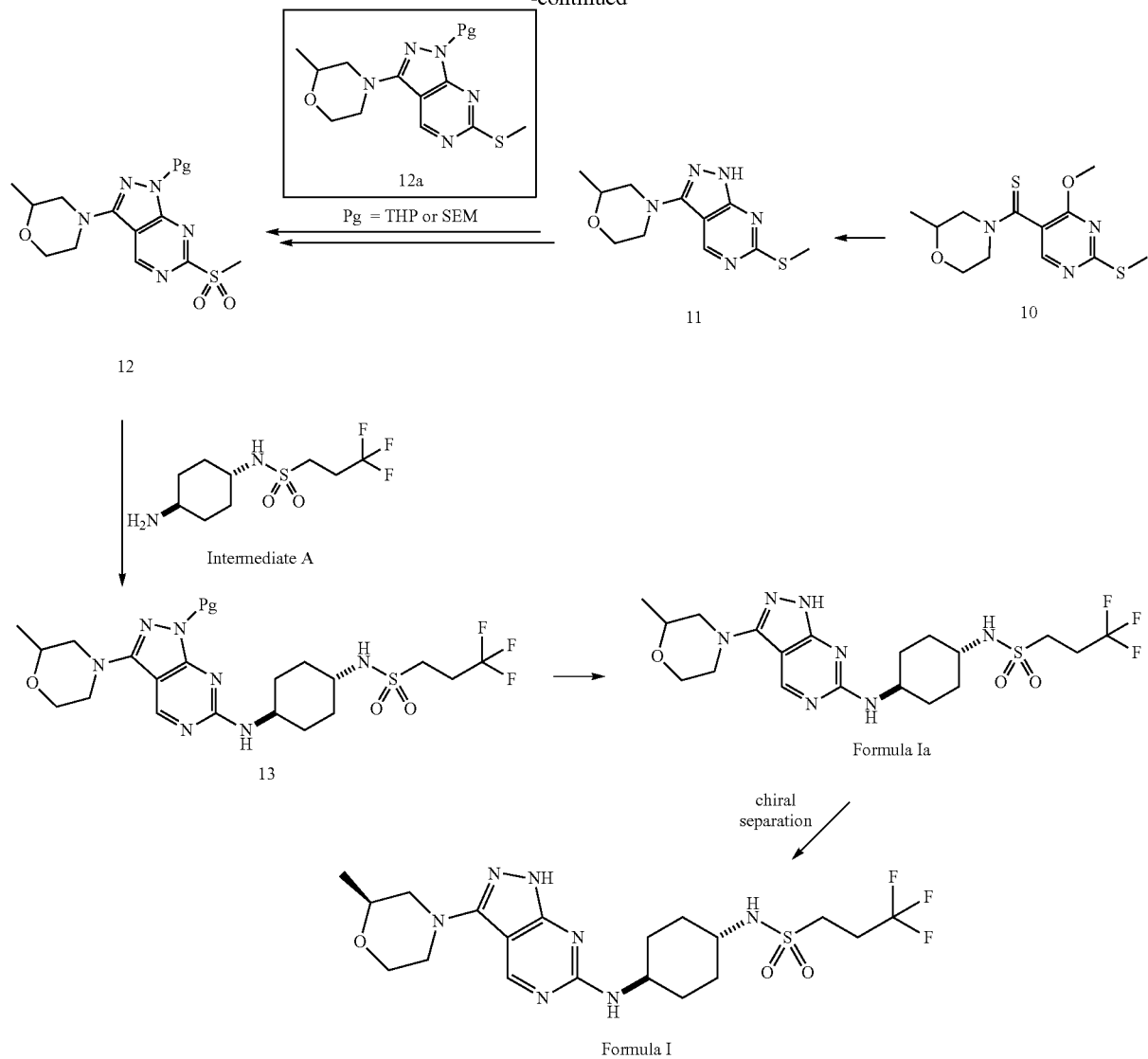
The general procedures which may be used to synthesise intermediate A are summarised in reaction Scheme 3.
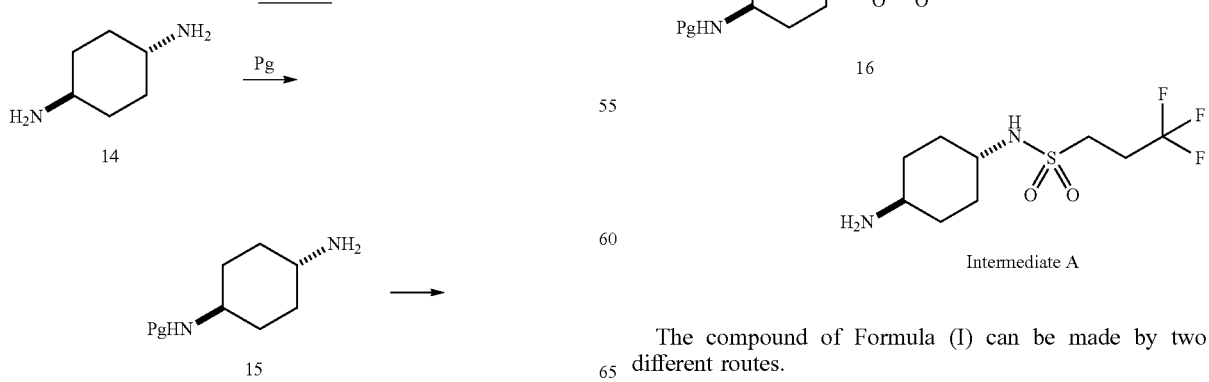
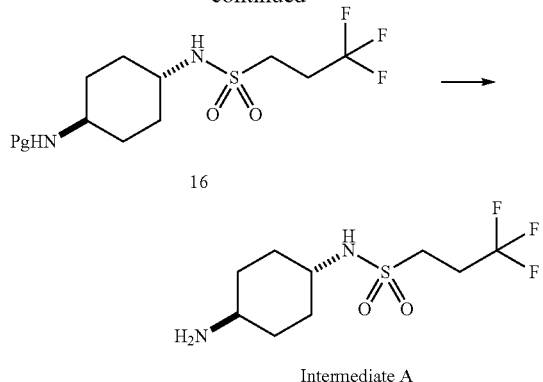
The compound of Formula (I) can be made by two different routes.
Scheme 1: Starting from 2,4-dihydroxypyrimidine-5-carboxylic acid (1) which may be subjected to chlorination, amide formation with 2-methylmorpholine and displacement of the desired pyrimidine chloro with methoxide (OMe) followed by reaction with Intermediate A to give (5). The two final steps involve formation of a thiol amide and cyclisation with hydrazine followed by chiral separation to give the compound of Formula (I).

It will be appreciated by the skilled artisan that in order to obtain one enantiomer of the compound of Formula (I), 2-methylmorpholine (Intermediate B) may be employed as a mixture of enantiomers as shown in Scheme 1, in which case any of the subsequent compounds with the morpholine moiety shown in Scheme 1 (including Formula (I) itself as shown in Scheme 1) may be subjected to chiral separation, to give rise to the desired enantiomer of Formula (I) at the end of the synthesis. Alternatively, 2-methyl morpholine (Intermediate B) may be employed as a single enantiomer (e.g. the S enantiomer, Intermediate B*) in the reaction where it is introduced, to give rise to only one enantiomer of Formula (I) at the end of the synthesis.

Scheme 2: Starting from ethyl 4-chloro-2-(methylthio) pyrimidine-5-carboxylate (7) this compound may be subjected to hydrolysis, then displacement with Ethoxide (OEt) followed by amide formation with 2-methylmorpholine to give (9). The amide (9) may be converted to the thiol amide (10) then cyclised with hydrazine to give (11). The pyrazole NH of (11) may be protected with a suitable protecting group such as THP or SEM, followed by oxidisation of the thiol to sulfoxide in the presence of a suitable reagent such as hydrogen peroxide ($H_2O_2$) to provide compound (12). The sulfoxide may be displaced with intermediate A to give (13) followed by deprotection and chiral separation to yield the compound of Formula (I).

It will be similarly appreciated that in order to obtain a single enantiomer of the compound of Formula (I), either 2-methylmorpholine (Intermediate B) may be employed as a single enantiomer (e.g. the S enantiomer, Intermediate B*) in Scheme 2 or chiral separation of any of the subsequent intermediates or final compound of Formula (I) (as shown in Scheme 2) may be carried out.

Scheme 3: Intermediate A in Scheme 3 may be made from cyclohexane-1,4-diamine (14). Compound (14) may be protected with a suitable protecting group (Pg) (such as Boc) to give compound (15) followed by sulfonylation of the remaining free $NH_2$ to give (16). Compound (16) may then be deprotected under suitable conditions to give Intermediate A.

Compounds (1, Alfa Aesar), (7, Alfa Aesar) and (14, Aldrich Sigma) are commercially available.

Examples of other protecting groups (Pg) that may be employed in the synthetic routes described herein and the means for their removal can be found in T. W. Greene 'Protective Groups in Organic Synthesis', 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

Methods of Use

It will be appreciated by those skilled in the art that references herein to treatment refer to the treatment of established conditions. However, the compounds of Formula (I) and pharmaceutically acceptable salts thereof may, depending on the condition, also be useful in the prevention (prophylaxis) of certain diseases.

As used herein, unless otherwise indicated, "treat", "treating" or "treatment" in reference to a disease means: (1) to ameliorate the disease or one or more of the biological manifestations of the disease (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, unless otherwise indicated, "prevent", "preventing" or "prevention" means the prophylactic administration of a drug to diminish the likelihood of the onset of or to delay the onset of a disease or biological manifestation thereof. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

Thus, in one embodiment, there is provided the treatment or prevention of a disease. In another embodiment, there is provided the treatment of a disease. In a further embodiment, there is provided the prevention of a disease.

There is thus provided as a further aspect of the invention a compound of Formula (I), or a pharmaceutically acceptable salt thereof, for use in therapy.

It will be appreciated that, when a compound of Formula (I) or a pharmaceutically acceptable salt thereof is used in therapy, it is used as an active therapeutic agent.

There is also therefore provided a compound of Formula (I), or a pharmaceutically acceptable salt thereof, for use in the treatment or prevention of leishmaniasis, particularly visceral leishmaniasis.

There is further provided the use of a compound of Formula (I), or a pharmaceutically acceptable salt thereof, in the manufacture of a medicament for the treatment or prevention of leishmaniasis, particularly visceral leishmaniasis.

There is further provided a method of treatment or prevention of leishmaniasis, particularly visceral leishmaniasis, which method comprises administering to a human subject in need thereof, a therapeutically effective amount of a compound of Formula (I), or a pharmaceutically acceptable salt thereof.

Compositions and Formulations

While it is possible that, for use in the methods of the invention, the compound of Formula (I), or a pharmaceutically acceptable salt thereof, or a compound of Formula (II), (III), or (IV), or a pharmaceutically acceptable salt thereof, may be administered as the bulk substance, it is usually preferable to present the active ingredient in a pharmaceutical formulation, for example, wherein the agent is in admixture with at least one pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise, in addition to the carrier, any suitable binder(s), lubricant(s), suspending agent(s), coating agent(s), and/or solubilizing agent(s).

The phrase "pharmaceutically acceptable", as used herein, refers to salts, molecular entities and other ingredients of compositions that are generally physiologically tolerable and do not typically produce untoward reactions when administered to a mammal (e.g., human). Suitably, as used herein, the term "pharmaceutically acceptable" means approved by a regulatory agency of the Federal or a state government for use in mammals, and more particularly in humans, or listed in the U.S. Pharmacopoeia or other generally recognized texts, for example the International Union of Pure and Applied Chemistry (IUPAC) Handbook of Pharmaceutical Salts, 2011 Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine, by analogy with formulation of antibacterials, such as anti-tubercular agents, or formulation of antimalarial agents.

The compounds of the invention will normally, but not necessarily, be formulated into pharmaceutical compositions prior to administration to a patient. In one aspect, the invention is directed to a pharmaceutical composition comprising a compound of Formula (I), or a pharmaceutically acceptable salt thereof. In another aspect the invention is directed to a pharmaceutical composition comprising a compound of Formula (I), or a pharmaceutically acceptable salt thereof, together with at least one pharmaceutically acceptable carrier. In a further aspect, the invention is directed to a pharmaceutical composition comprising a compound of Formula (II), (III), or (IV) together with at least one pharmaceutically acceptable carrier. The carrier must be "acceptable" in the sense of being compatible with the other ingredients of the formulation and not deleterious to the recipient thereof.

A therapeutically effective amount of the compound of the present invention can be determined by methods known in the art. The therapeutically effective quantities will depend on the age and on the general physiological condition of the subject, the route of administration and the pharmaceutical formulation used. The therapeutic doses will generally be between about 1 and 2000 mg/day, for example between about 500 and 2000 mg/day. The daily dose as employed for human treatment will range from 1 to 2000 mg, which may be administered in one or two daily doses, for example, depending on the route of administration and the condition of the subject. When the composition comprises dosage units, each unit will contain 1 mg to 2 g of active ingredient. When the dosage form is a tablet, the total weight of the tablet is suitably 1000 mg or lower.

The present invention is further related to a pharmaceutical composition comprising a compound of Formula (I), or a pharmaceutically acceptable salt thereof.

The present invention is further related to a pharmaceutical composition for the treatment of leishmaniasis, particularly visceral leishmaniasis (VL), comprising the compound of Formula (I) or a pharmaceutically acceptable salt thereof.

The present invention is yet further related to a pharmaceutical composition comprising a compound of Formula (I), or a pharmaceutically acceptable salt thereof together with at least one pharmaceutically acceptable carrier.

The present invention is even further related to a pharmaceutical composition comprising a) a compound of Formula (I) or a pharmaceutically acceptable salt thereof, and b) one or more pharmaceutically acceptable carriers.

The present invention is even further related to a pharmaceutical composition comprising a) 1 to 2000 mg of the compound of Formula (I) or a pharmaceutically acceptable salt thereof, and b) 1 and 2000 mg of one or more pharmaceutically acceptable carriers.

The present invention is yet further related to a pharmaceutical composition comprising a compound of Formula (II), (III), or (IV) or a pharmaceutically acceptable salt thereof, together with at least one pharmaceutically acceptable carrier.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients. In one aspect, the pharmaceutical composition is formulated for oral administration.

The pharmaceutical compositions of the invention include those in a form adapted for oral use in mammals including humans.

The pharmaceutical compositions of the invention include those in a form adapted for oral use and may be used for the treatment of leishmaniasis, particularly visceral leishmaniasis, in mammals including humans.

The compound of the invention can be administered for immediate-, delayed-, modified-, sustained-, pulsed- or controlled-release applications.

The composition may be formulated for administration by any convenient route. For the treatment of leishmaniasis, particularly visceral leishmaniasis (VL), the compositions may be in the form of tablets, capsules, powders, granules, lozenges, aerosols or liquid preparations, for oral use.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

The compound of Formula (I), (II), (III), or (IV), or a pharmaceutically acceptable salt thereof, may be the sole therapeutic agent in the compositions of the invention, or it may be present in the formulation in combination with one or more additional therapeutic agents.

The invention thus provides in a further aspect, a combination comprising (a) a compound of Formula (I), or a pharmaceutically acceptable salt thereof, and (b) at least one additional therapeutic agent. The combination optionally further comprises at least one pharmaceutically acceptable carrier. In one aspect of the invention there is provided a pharmaceutical composition comprising a compound of Formula (I), or a pharmaceutically acceptable salt thereof, together with at least one pharmaceutically acceptable carrier and one or more additional therapeutic agents.

The invention further provides a combination comprising (a) a compound of Formula (II), (III), or (IV), or a pharmaceutically acceptable salt thereof, and (b) at least one additional therapeutic agent. The combination optionally further comprises at least one pharmaceutically acceptable carrier. In one aspect of the invention there is provided a pharmaceutical composition comprising a compound of Formula (II), (III), or (IV), or a pharmaceutically acceptable salt thereof, together with at least one pharmaceutically acceptable carrier and one or more additional therapeutic agents.

Examples of such one or more additional therapeutic agents are anti-leishmania agents, including, but not limited to, miltefosine, paromomycin, sodium stibugluconate, meglumine antimoniate, amphotericin B deoxycholate or liposomal amphotericin B. In one aspect of the invention for oral treatment the additional therapeutic agent is miltefosine. Such chemotherapy is determined by the judgment of the treating physician using preferred drug combinations. In addition to the aforementioned, future anti-leishmania therapeutic agents emerging from clinical studies may also be employed as the one or more additional therapeutic agents in a combination with a compound of Formula (I).

In another aspect, the invention provides a combination comprising a compound of Formula (I) or a pharmaceutically acceptable salt thereof, together with one or more additional therapeutic agents, such as an anti-leishmaniasis agent, an anti-AIDS or anti-HIV agent, or an anti-TB agent.

In yet another aspect, the invention provides a combination comprising a compound of Formula (II), (III), or (IV), or a pharmaceutically acceptable salt thereof, together with one or more additional therapeutic agents, such as an anti-leishmaniasis agent, an anti-AIDS or anti-HIV agent, or an anti-TB agent.

In a further aspect, the one or more additional therapeutic agent is, for example, an agent useful for the treatment of leishmaniasis in a mammal, therapeutic vaccines, anti-leishmaniasis agents and/or agents for the treatment of HIV/AIDS.

The compounds of Formula (I), (II), (III), or (IV), or a pharmaceutically acceptable salt thereof, and further therapeutic agent(s) may be employed in combination by administration simultaneously in a unitary pharmaceutical composition including both agents. Alternatively, the combination may be administered separately in separate pharmaceutical compositions, each including one of the agents in a sequential manner wherein, for example, the compound of Formula (I), (II), (III), or (IV), or a pharmaceutically acceptable salt thereof is administered first and the other agent second and vice versa. Such sequential administration may be close in time (e.g. simultaneously) or remote in time. For example, administration of the other agent several minutes to several dozen minutes after the administration of the first agent, and administration of the other agent several hours to several days after the administration of the first agent are within the scope of the invention, wherein the lapse of time is not limited. For example, one agent may be administered once a day, and the other agent may be administered 2 or 3 times a day, or one agent may be administered once a week, and the other agent may be administered once a day.

When administration is sequential, either the compound of the present invention or one or more additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

During a treatment regime, it will be appreciated that administration of each agent of the combination may be repeated one or more times.

Furthermore, the agents may be administered in the same or different dosage forms, e.g. one agent may be administered topically and the other compound may be administered orally. Suitably, both agents are administered orally.

The combinations may be presented as a combination kit. By the term "combination kit" "or kit of parts" as used herein is meant the pharmaceutical composition or compositions that are used to administer the combination according to the invention. When the agents of the combination are administered simultaneously, the combination kit can contain the agents in a single pharmaceutical composition, such as a tablet, or in separate pharmaceutical compositions. When the agents are not administered simultaneously, the combination kit will contain each agent in separate pharmaceutical compositions either in a single package or in separate pharmaceutical compositions in separate packages. The combination kit can also be provided with instructions, such as dosage and administration instructions. Such dosage and administration instructions can be of the kind that are provided to a doctor, for example by a drug product label, or they can be of the kind that are provided by a doctor, such as instructions to a patient.

In one aspect, the one or more additional therapeutic agent is a therapeutic vaccine. A compound of Formula (I), or a pharmaceutically acceptable salt thereof, may thus be administered in conjunction with vaccination against leishmaniasis infection. Existing veterinary vaccines include canileish and leishmune.

The compound of Formula (I), or a pharmaceutically acceptable salt thereof, may be either i) administered to an individual who has previously been vaccinated against leishmaniasis infection; ii) administered to an individual who is subsequently vaccinated against leishmaniasis infection; or iii) may be co-administered with a vaccine against leishmaniasis infection, either by administering the compound of the invention and the vaccine together in the same dosage form or co-administering the compound of the invention and the vaccine in separate dosage forms.

When a compound of Formula (I), or a pharmaceutically acceptable salt thereof is used in combination with one or more additional therapeutic agents, the dose of the compound or agent may differ from that when the compound or agent is used alone. Appropriate doses will be readily appreciated by those skilled in the art. It will be appreciated that the amount of a compound of the invention and the one or more additional therapeutic agents required for use in treatment will vary with the nature of the condition being treated and the age and the condition of the patient and will be ultimately at the discretion of the attendant physician or veterinarian.

Abbreviations

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:
ACN Acetonitrile
AIDS Acquired Immune Deficiency Syndrome
Boc tert-butyloxycarbonyl
aq. Aqueous
$CDCl_3$ Deuterated chloroform
$CD_3OD$ Deuterated methanol
$CO_2$ Carbon dioxide
Conc. Concentrated
Cu Kα Copper K-alpha
DAD Diode array detection
DAPI 4',6-Diamidino-2-phenylindole
DCM Dichloromethane
DIPEA Diisopropylethylamine
DMF N,N-Dimethylformamide
DMSO Dimethylsulfoxide
DMSO-$d_6$ Deuterated dimethylsulfoxide
DSC Differential scanning calorimetry
ee enantiomeric excess
$Et_2O$ Diethyl ether
EtOAc Ethyl acetate
EtOH Ethanol
FT Fourier transform
g grams
Ge Germanium
h hours
$H_2$ Hydrogen
$H_2O$ Water
HCl Hydrochloric acid
HIV Human Immunodeficiency Virus
HPLC high performance liquid chromatography
HPMCAS Hydroxypropylmethyl cellulose acetate succinate
InGaAs Indium gallium arsenide
L liters
Lawesson's reagent 2,4-Bis(4-methoxyphenyl)-1,3,2,4-dithiadiphosphetane-2,4-disulfide
M Molar
MeOH Methanol
min Minutes
mL Milliliter
mmol Millimolar
MOM Methoxymethyl ether
MS Mass spectrum
$Na_2CO_3$ Sodium bicarbonate
$NaHCO_3$ Sodium hydrogen carbonate
$NaHSO_3$ Sodium bisulfite or Sodium hydrogen sulfite
$Na_2SO_4$ Sodium sulfate
NaOH Sodium hydroxide
Nd Neodymium
$NH_4OH$ Ammonium Hydroxide
NMR Nuclear Magnetic Resonance spectroscopy
PBS Phosphate buffered saline
PBS-A Bovine serum albumin
Pd/C Palladium on Carbon
Pg Protecting group
PMA Phorbol 12-myristate 13-acetate
PXRD Powder X-ray diffraction
quant. Quantitative
RT Room Temperature
RTMS Real Time Multi-Strip
sat. Saturated
SEM 2-(Trimethylsilyl)ethoxy]methyl
$SOCl_2$ thionyl chloride
sol. Solution
ssNMR solid state nuclear magnetic resonance
TFA Trifluoroacetic acid
TGA Thermogravimetric Analysis
THF Tetrahydrofuran
THP Tetrahydropyranyl
TLC Thin layer chromatography
wt % Weight percentage
$YVO_4$ Yttrium orthovanadate
2θ 2 theta angles

EXAMPLES

The following Examples illustrate the invention, as guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (ppm) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides (including sodium hydride) and organo-metallic reagents are carried out under argon or nitrogen unless otherwise specified.

In the following Intermediates and Examples, where the relative stereochemistry of the compound has been identified, this is indicated both in the name and structure of the compound.

In certain of the following Intermediates and Examples, starting materials are identified by reference to other Intermediate or Example numbers. This does not signify that the actual material (or "batch") obtained from any particular Intermediate or Example was necessarily used in a subsequent step exemplified herein, but is used as a short-hand means of denoting the relevant compound name.

INTERMEDIATES

Intermediate A, TFA Salt: N-((1,4-trans)-4-aminocyclohexyl)-3,3,3-trifluoropropane-1-sulfonamide, TFA Salt

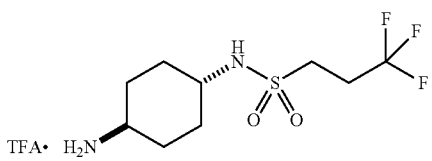 [SMILES: N[C@H]1CC[C@H](NS(=O)(=O)CCC(F)(F)F)CC1 ; "TFA·"]

(a) tert-Butyl ((1,4-trans)-4-aminocyclohexyl)carbamate (Compound 15, Scheme 3, Wherein Pg is Boc)

In a 10 L reactor, a solution of (1,4-trans)-cyclohexane-1,4-diamine (compound 14, Scheme 3) (89 g, 779 mmol, Aldrich Sigma) in Et$_2$O (2 L) was cooled to 5° C., then a solution of di-tert-butyl dicarbonate (170 g, 779 mmol) in Et$_2$O (1 L) was added dropwise over 2 h. The reaction mixture was stirred at 5° C. for 2 h and at RT overnight. To the reaction mixture, 10% citric acid solution (3 L) was added and stirred for 30 min. The insoluble solid was filtered off, and the phases were separated. The aqueous layer was washed with Et$_2$O (1 L). The aqueous phase was cooled to 10° C. and basified with solid NaOH (pH 14), then extracted with DCM (2×2 L). The combined organic phases were dried over Na$_2$SO$_4$ and evaporated under reduced pressure to give a white solid (110 g, 66% yield).

This was combined with another batch (210 g) of this compound (compound 15) then re-purified by flash column chromatography (2-5% MeOH/DCM) to afford a white solid (compound 23) (297 g).

$^1$H NMR (400 MHz, CDCl$_3$) δ4.48-4.28 (1H, m), 3.48-3.28 (1H, m), 2.68-2.57 (1H, m), 2.01-1.89 (2H, m), 1.89-1.69 (2H, m), 1.35 (9H, s) and 1.28-1.05 (4H, m).

(b) tert-butyl ((1,4-trans)-4-(3,3,3-trifluoropropyl-sulfonamido)-cyclohexyl)carbamate (Compound 16)

This reaction was performed in two batches. To a suspension of tert-butyl ((1,4-trans)-4-aminocyclohexyl)carbamate (compound 15, wherein Pg is tert-butyl) (30 g, 140 mmol) in THF (1.33 L), cooled at −78° C., n-butyllithium (56 mL, 140 mmol) was added dropwise. The resulting mixture was stirred at −78° C. for 20 min and at −10° C. for 10 min. After cooling to −78° C., 3,3,3-trifluoropropane-1-sulfonyl chloride (17.64 mL, 140 mmol, purchased from Matrix) was added. After stirring for 1.5 h, it was allowed to warm to RT and stirred for 20 min. The reaction mixture was diluted with H$_2$O (500 mL), followed by addition of a solution 2M HCl (20 mL) and was extracted with EtOAc (400 mL). The organic layer was dried over Na$_2$SO$_4$, filtered and concentrated to give a white solid (43.5 g, 83% yield).

$^1$H NMR (400 MHz, DMSO-d$_6$) δ7.33 (1H, d), 6.77-6.70 (1H, m), 3.30-3.23 (2H, m), 3.17-3.01 (2H, m), 2.70-2.56 (2H, m), 1.87-1.67 (4H, m), 1.36 (9H, s) and 1.31-1.13 (4H, m).

(c) N-((1,4-trans)-4-aminocyclohexyl)-3,3,3-trifluoropropane-1-sulfonamide, TFA Salt (Intermediate A, TFA Salt)

TFA (182 mL, 2377 mmol) was added to a solution of tert-butyl ((1,4-trans)-4-(3,3,3-trifluoropropylsulfonamido) cyclohexyl)carbamate (compound 16) (89 g, 238 mmol) in DCM (732 mL), cooled to 0° C. The reaction mixture was stirred at RT overnight. The mixture was concentrated to dryness and co-evaporated with Et$_2$O (100 mL) to give a white solid (Intermediate A, TFA salt) (93.5 g, quant. yield).

$^1$H NMR (400 MHz, DMSO-d$_6$) δ7.89 (3H, br s), 7.43 (1H d), 3.34-3.24 (2H, m), 3.16-3.05 (1H, m), 2.99-2.86 (1H, m), 2.72-2.56 (2H, m), 1.95-1.84 (4H, m) and 1.43-1.21 (4H, m).

Intermediate B* [Intermediate B (S) Enantiomer], Hydrochloride Salt: (S)-2-methylmorpholine hydrochloride

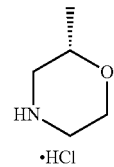

Intermediate B is commercially available as the free base or the hydrochloride, both as a racemic mixture and as each single enantiomer. It may alternatively be made as the S enantiomer, (Intermediate B*) in the form of its hydrochloride salt according to the method below.

(a) (S)-1-(benzyl(2-hydroxyethyl)amino)propan-2-ol 2-(benzylamino)ethan-1-ol (1.88 mL, 13.22 mmol, Aldrich) and (S)-2-methyloxirane (1.4 mL, 19.84 mmol, Aldrich) were mixed and the resulting mixture heated at 100° C. in a microwave oven for 1 h. Excess of (S)-2-methyloxirane was removed under vacuum to afford desired (S)-1-[benzyl(2-hydroxyethyl)amino]propan-2-ol as a colourless oil (2.77 g, quant. yield).

$^1$H NMR (400 MHz, DMSO-d$_6$) δ7.39-7.19 (5H, m), 4.42-4.35 (1H, m), 4.32-4.28 (1H, m), 3.77-3.65 (1H, m), 3.52-3.38 (2H, m), 2.60-2.46 (2H, m), 2.43-2.29 (2H, m) and 1.01 (3H, d).

(b) (S)-2-methyl-4-(4-nitrobenzenesulfonyl)morpholine (S)-1-(benzyl(2-hydroxyethyl)amino)propan-2-ol (10.62 g, 50.74 mmol) in MeOH (100 mL) was hydrogenated in the presence of Pd/C (2.7 g). The reaction was stirred at RT at atmospheric pressure under $H_2$ for 3 h. The mixture was filtered and concentrated to dryness to give crude (S)-1-((2-hydroxyethyl)amino)propan-2-ol that was used in the next step without further purification.

4-nitrobenzensulfonyl chloride (22.32 g, 100.7 mmol) was added portionwise to a stirred solution of the above product (6 g) and triethylamine (17.5 mL, 126 mmol) in DCM (100 mL). The resulting mixture was stirred at RT overnight then washed with 0.5 M HCl, $H_2O$ and brine. The organic phase was dried over $Na_2SO_4$, filtered and concentrated. The remaining residue was purified by flash column chromatography (Cyclohexane/EtOAc from 80/20 to 50/50) to afford desired (S)-2-methyl-4-(4-nitrobenzenesulfonyl)morpholine (8.2 g, 57% yield).

Enantioselectivity determined using a chiral column: 250 mm Chiralpak AD-H, 4.6 mm i.D., n-Hexane/EtOH=30/70, 0.8 mL/min, 298K, 220 nm. First enantiomer (major) Rt=13.7 min, second enantiomer (minor) Rt=19.1 min. ee measured: 96%

$^1$H NMR (400 MHz, DMSO-$d_6$) δ8.48 (2H, d), 8.02 (2H, d), 3.86-3.80 (1H, m), 3.61-3.47 (4H, m), 2.39-2.30 (1H, m), 2.07-1.98 (1H, m) and 1.06 (3H, d).

(c) (S)-2-methylmorpholine hydrochloride

To a solution of (S)-2-methyl-4-(4-nitrobenzenesulfonyl)morpholine (1 g, 3.5 mmol) and Lithium hydroxide monohydrate (0.586 g, 13.97 mmol) in ACN (35 mL) was added 1-propanthiol (1.26 mL, 13.97 mmol) at RT and the resultant mixture stirred overnight. 1.25M HCl in MeOH (5 eq.) was added. The volatiles were removed under vacuum to give crude (S)-2-methylmorpholine hydrochloride. This solid residue was repeatedly washed with cyclohexane to remove apolar by-products, affording (S)-2-methylmorpholine hydrochloride (Intermediate B*) which was used in the next step without further purification.

MS (+ve ion electrospray): m/z 102 [MH$^+$]

Intermediate C, 2-((di-tert-butoxyphosphoryl)oxy)ethyl (2,5-dioxopyrrolidin-1-yl) carbonate

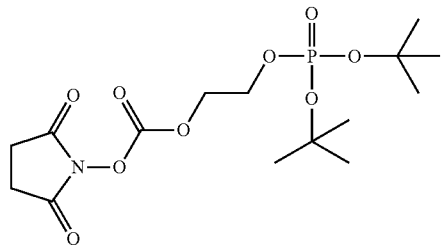 [SMILES: CC(C)(C)OP(=O)(OCCOC(=O)ON1C(=O)CCC1=O)OC(C)(C)C]

(a) di-tert-butyl (2-hydroxyethyl) phosphate

To a solution of di-tert-butyl hydrogen phosphate, potassium salt (15 g, 60.2 mmol, Aldrich) in DMF (100 mL), 2-bromoethanol (7.52 g, 60.2 mmol, Aldrich) was added. The resulting mixture was heated at 80° C. overnight.

The reaction was poured into water (250 mL) and extracted with EtOAc (3×250 mL). The organic layer was dried over $Na_2SO_4$, filtered, concentrated under reduced pressure and the residue was purified by flash column chromatography (0-5% MeOH/DCM) to afford desired di-tert-butyl (2-hydroxyethyl) phosphate as a colorless oil (8 g, 52.3%).

$^1$H NMR (400 MHz, DMSO-$d_6$) δ: 4.83-4.77 (1H, m), 3.86-3.80 (2H, m), 3.58-3.51 (2H, m), 1.42 (18H, s)

(b) 2-((di-tert-butoxyphosphoryl)oxy)ethyl (2,5-dioxopyrrolidin-1-yl) carbonate To a mixture of di-tert-butyl (2-hydroxyethyl) phosphate (8 g, 31.5 mmol) in acetonitrile (160 mL), triethylamine (13.16 mL, 94 mmol) and bis(2,5-dioxopyrrolidin-1-yl) carbonate (12.09 g, 47.2 mmol, Acros) were added. The resulting yellow solution was stirred at RT for 3 h.

The reaction mixture was evaporated under reduced pressure and the residue was dissolved in DCM (300 mL) and washed with water (2×150 mL). The organic layer was dried over $Na_2SO_4$, filtered and concentrated under reduced pressure to give desired 2-((di-tert-butoxyphosphoryl)oxy)ethyl (2,5-dioxopyrrolidin-1-yl) carbonate (Intermediate C) as a pale brown solid (12 g, 96%).

$^1$H NMR (400 MHz, DMSO-$d_6$) δ: 4.55-4.49 (2H, m), 4.16-4.09 (2H, m), 2.81 (4H, s), 1.41 (18H, s)

Final Compounds

Example 1

Polymorphic Forms 1 and 2 of 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Formula (I))

and

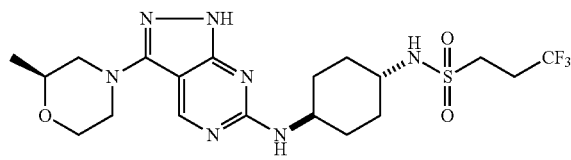

3,3,3-trifluoro-N-((1,4-trans)-4-((3-((R)-2-methyl-morpholino)-1H-pyrazolo[3,4-d]pyrimidin-6-yl)amino)cyclohexyl)propane-1-sulfonamide (opposite enantiomer of Formula (I)

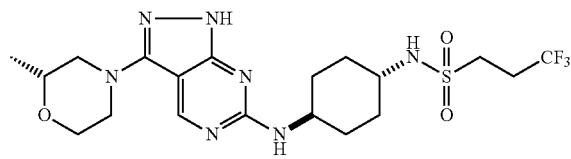

Example 1 Method A

(a) (2,4-dichloropyrimidin-5-yl)(2-methylmorpholino)methanone (Compound 3)

Phosphorus pentachloride (128.1 g, 0.615 mol) was added portionwise to a stirred mixture of 2,4-dihydroxypyrimidine-5-carboxylic acid (compound 1) (26.7 g, 171 mmol, Alfa Aesar) in phosphorous oxychloride (122.2 mL, 1.29 mol) at RT. The reaction mixture was heated to 115° C. and stirred overnight. The reaction was cooled to RT and the volatiles were removed under vacuum. The residue was diluted with cyclohexane and filtered. The filtrate was evaporated under reduced pressure to give 2,4-dichloropyrimidine-5-carbonyl chloride (compound 2) as a yellow oil (37.9 g). This material was used in the next step without further purification.

A solution of 2-methylmorpholine (Intermediate B) (4.91 g, 48.6 mmol, Enamine) and DIPEA (8.5 mL, 48.8 mmol) in DCM (60 mL) was added dropwise over 30 minutes to a stirred solution of 2,4-dichloropyrimidine-5-carbonyl chloride (compound 2) (9.34 g, 44.2 mmol) in DCM (242 mL) at 0° C. The reaction mixture was stirred for 2 h at 0° C. and then quenched with $H_2O$. The phases were separated and the organic phase washed with 0.5 M HCl, $H_2O$, dried over $Na_2SO_4$ and then evaporated under reduced pressure. The residue was purified by flash column chromatography (Cyclohexane/EtOAc 6/4 to 4/6) to give desired (2,4-dichloropyrimidin-5-yl)(2-methylmorpholino)methanone (compound 3) as a colourless oil which solidified on standing (11.02 g, 90% yield).

It will be appreciated by the skilled artisan that the above reaction may be carried out using 2-methylmorpholine hydrochloride salt (Intermediate B, hydrochloride salt), in which case an extra one equivalent of base (DIPEA) may be used in the reaction. Alternatively, 2-methylmorpholine hydrochloride salt may be converted to 2-methylmorpholine free base by treatment with a suitable base (e.g. DIPEA) prior to being employed in the reaction.

MS (+ve ion electrospray): m/z 276 [MH$^+$]

(b) 3,3,3-trifluoro-N-((1,4-trans)-4-((4-methoxy-5-(2-methylmorpholine-4-carbonyl)pyrimidin-2-yl) amino)cyclohexyl)propane-1-sulfonamide (Compound 5)

Sodium methoxide (3.1 g, 57.4 mmol) was added to a stirred solution of 4-(2,4-dichloropyrimidine-5-carbonyl)-2-methylmorpholine (compound 3) (13.72 g, 49.7 mmol) in dry THF (248 mL) at −40° C. The reaction mixture was stirred for 30 min at −40° C. and then slowly allowed to warm to −10° C. Further sodium methoxide (300 mg, 5.55 mmol) was added at −10° C. and the reaction mixture was stirred for 20 min at this temperature. The reaction mixture was quenched with sat. aq. sol. ammonium chloride solution and extracted with EtOAc (3×). The combined organic phases were evaporated under reduced pressure. The resulting crude material (15 g) was purified by flash column chromatography (cyclohexane/EtOAc from 6/4 to 3/7) to give (2-chloro-4-methoxypyrimidin-5-yl)(2-methylmorpholino)methanone (compound 4) (9.22 g, 68% yield). This material was used in the next step without further purification.

(2-chloro-4-methoxypyrimidin-5-yl)(2-methylmorpholino)methanone (compound 4) (9.22 g, 33.9 mmol) and Intermediate A, TFA salt (12.76 g, 32.9 mmol) were combined and dissolved in dry dioxane (283 mL). DIPEA (23.6 mL, 135.5 mmol) was added and the resulting mixture was stirred at 100° C. for 48 h. The solvent was removed under vacuum to afford crude material which was purified by flash column chromatography (DCM/EtOAc/MeOH 75/20/5) to afford 3,3,3-trifluoro-N-((1,4-trans)-4-((4-methoxy-5-(2-methylmorpholine-4-carbonyl)pyrimidin-2-yl)amino)cyclohexyl)propane-1-sulfonamide (compound 5) (6.89 g, 40% yield).

MS (+ve ion electrospray): m/z 510 [MH$^+$]

(c) 3,3,3-trifluoro-N-((1,4-trans)-4-((4-methoxy-5-(2-methylmorpholine-4-carbonothioyl)pyrimidin-2-yl)amino)cyclohexyl)propane-1-sulfonamide (Compound 6)

3,3,3-trifluoro-N-((1,4-trans)-4-((4-methoxy-5-(2-methylmorpholine-4-carbonyl)pyrimidin-2-yl)amino)cyclohexyl)propane-1-sulfonamide (compound 5) (6.81 g, 13.4 mmol) was dissolved in dry THF (250 mL). Lawesson's reagent was added in one portion (9.47 g, 23.4 mmol) and the resulting mixture was stirred for 2 h at 45° C. The reaction mixture was quenched by addition of EtOAc and sat. aq. sol. NaHCO$_3$. The layers were separated and the aqueous extracted with EtOAc (2×). The combined organic layers were washed with brine and dried over Na$_2$SO$_4$. The solvent was removed under vacuum to afford a crude product which was purified by flash column chromatography (DCM/Cyclohexane/EtOAc/MeOH 37.5/37.5/20/5) to afford 3,3,3-trifluoro-N-((1,4-trans)-4-((4-methoxy-5-(2-methylmorpholine-4-carbonothioyl)pyrimidin-2-yl)amino)cyclohexyl)propane-1-sulfonamide (compound 6) (6.25 g, 89% yield) as a yellowish solid.

MS (+ve ion electrospray): m/z 526 [MH$^+$]

(d) 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Formula I)

3,3,3-trifluoro-N-((1,4-trans)-4-((4-methoxy-5-(2-methylmorpholine-4-carbonothioyl)pyrimidin-2-yl)amino)cyclohexyl)propane-1-sulfonamide (compound 6) (6.25 g, 11.9 mmol) was dissolved in dioxane (80 mL), then hydrazine hydrate 55% (23 mL, 238 mmol) was added and the reaction stirred at 90° C. for 2 days. The solvent was removed under vacuum to afford a crude solid which was purified by flash column chromatography (DCM/EtOAc/MeOH 75/20/5) to obtain the compound of Formula Ia, which is a racemic mixture of the compound of Formula I and its opposite enantiomer.

Characterisation of Formula Ia (racemic mixture):
MS (+ve ion electrospray): m/z 492 [MH$^+$]

The single enantiomers of racemic mixture Formula Ia were obtained by chiral separation using preparative chiral HPLC: Chiralpak IA (25×3 cm), 5 mm, EtOH/MeOH/DCM 45/45/10+0.1% iso-Propanol, flow rate 36 mL/min, DAD detection 220 nm, sample dissolved in MeOH/DCM 1/1 (13 mg/mL), 57 mg sample each injection. The separation led to these amounts: Enantiomer 1 (1.888 g, ee>99%, 32.2% yield) and Enantiomer 2 (compound of Formula I) (2.015 g, ee=98.6%, desired product, 34.4% yield). The enantiomeric excess of enantioenriched material was determined by chiral HPLC according to the following analytical method: 250 mm Chiralpak IA, 5 mm i.D., EtOH/MeOH/DCM=45/45/10+0.1% Isopropanol, 1 mL/min, 220 nm. Enantiomer 1, Rt=8.6 min; Enantiomer 2, Rt=13.2 min.

i) Characterisation of Enantiomer 2 (Compound of Formula (I)

$^1$H NMR (500 MHz, CDCl$_3$) δ 11.97 (1H, br s), 8.83 (1H, br s), 7.35 (1H, d), 7.19 (1H, br s), 3.87 (1H, dd), 3.73 (1H, d), 3.71-3.54 (4H, m), 3.36-3.26 (2H, m), 3.14 (1H, br s), 2.88-2.80 (1H, m), 2.71-2.61 (2H, m), 2.56-2.46 (1H, m), 1.96-1.88 (4H, m), 1.41-1.26 (4H, m) and 1.15 (3H, d).

MS (+ve ion electrospray): m/z 492 [MH$^+$]

ii) Characterisation of Enantiomer 1 (Opposite Enantiomer of Compound of Formula (I)

MS (+ve ion electrospray): m/z 492 [MH$^+$]

Polymorphic Form 1 of the Compound of Formula (I)

The compound of Formula (I) obtained using the above method (enantiomer 2) is polymorphic Form 1.

Polymorphic Form 2 of the Compound of Formula (I)

3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide, (Form 1, 10 mg, 0.02 mmol) was combined with water (1 ml). The suspension was stirred for 72 h while cycling the temperature between 40° C. and 5° C. The suspension was equilibrated (aged) at RT for 1 hr. The solids were isolated by vacuum filtration and air dried for 3 h to give 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide, Form 2.

Example 1 Method B (a) 4-ethoxy-2-(methylthio)pyrimidine-5-carboxylic acid (compound 8)

1M aq. NaOH (215 mL, 215 mmol) was added to a stirred suspension of ethyl 4-chloro-2-(methylthio)pyrimidine-5-carboxylate (compound 7) (25 g, 107.5 mmol, Alfa Aesar) in EtOH (512 mL). The reaction mixture was stirred at 50° C. for 3 h. After cooling at 0° C., conc. HCl (25 mL) was added. EtOH was evaporated under reduced pressure and the residue filtered, washed with H$_2$O (2×100 mL) and dried under vacuum at 45° C. overnight. From aqueous phase further precipitate was found which was filtered, washed with H$_2$O (2×50 mL) and dried in a vacuum oven at 40° C. overnight. Both solids were combined to give 4-ethoxy-2-(methylthio) pyrimidine-5-carboxylic acid (compound 8) (19.7 g, 85% yield).

MS (+ve ion electrospray): m/z 215 [MH$^+$]

(b) (4-ethoxy-2-(methylthio)pyrimidin-5-yl)(2-methylmorpholino)-methanone (Compound 9)

SOCl$_2$ (8.34 mL, 115 mmol) was added dropwise to a stirred solution of 4-ethoxy-2-(methylsulfanyl)pyrimidine-5-carboxylic acid (compound 8) (5 g, 23 mmol) in DCM (46 mL) at RT. The reaction mixture was stirred at 40° C. overnight. The reaction mixture was evaporated under reduced pressure, toluene (35 mL) added and the residue concentrated in vacuo several times (3×). The residue was diluted in dry THF (45 mL), DIPEA was added (4.9 mL, 28 mmol) and the reaction was cooled to 0° C. After 5 mins, 2-methylmorpholine (Intermediate B) (3.3 g, 32 mmol, commercially available from Enamine) was added. The reaction mixture was stirred at RT for 3 h. The reaction mixture was diluted in EtOAc (50 mL) and washed with H$_2$O (100 mL). The aqueous phase was extracted with EtOAc (3×40 mL) and the combined organic phases were washed with brine, dried over Na$_2$SO$_4$ and evaporated to give 5.3 g of crude material. This was used in next step without further purification.

MS (+ve ion electrospray): m/z 298 [MH$^+$]

It will be appreciated by the skilled artisan that the above reaction may be carried out using 2-methylmorpholine hydrochloride salt (Intermediate B, hydrochloride salt), in which case an extra one equivalent of base (DIPEA) may be used in the reaction. Alternatively, 2-methylmorpholine hydrochloride salt may be converted to 2-methylmorpholine free base by treatment with a suitable base (e.g. DIPEA) prior to being employed in the reaction.

(c) (4-ethoxy-2-(methylthio)pyrimidin-5-yl)(2-methylmorpholino)-methanethione (Compound 10)

Lawesson's reagent (12.5 g, 31 mmol) was added to a stirred suspension of (4-ethoxy-2-(methylthio)pyrimidin-5-yl)(2-methylmorpholino)methanone (compound 9) (5.3 g, 18 mmol) in THF (125 mL). The reaction mixture was heated at 45° C. and stirred for 1 h. The reaction mixture was diluted with EtOAc (125 mL) and washed with sat. aq. sol. Na$_2$CO$_3$ (250 mL). The aqueous phase was further extracted with EtOAc (3×100 mL). The combined organic phases were washed with brine, dried over Na$_2$SO$_4$ and evaporated under reduced pressure. The residue was purified by flash column chromatography (Cyclohexane/EtOAc 7/3) affording (4-ethoxy-2-(methylthio)pyrimidin-5-yl)(2-methylmorpholino)methanethione (compound 10) (4.48 g, 80% yield).

MS (+ve ion electrospray): m/z 314 [MH$^+$]

(d) 2-methyl-4-(6-(methylthio)-1H-pyrazolo[3,4-d]pyrimidin-3-yl)-morpholine (Compound 11)

Hydrazine hydrate (55% w/w, 8.1 mL, 143 mmol) was added to a stirred solution of (4-ethoxy-2-(methylthio)pyrimidin-5-yl)(2-methylmorpholino)methanethione (compound 10) (4.48 g, 14.3 mmol) in 1,4-dioxane (95 mL). The resulting mixture was stirred at 60° C. for 24 h. Further hydrazine hydrate was added (55% w/w, 4.1 mL, 72 mmol) and the reaction stirred for an additional 24 h at 60° C. The reaction was quenched with aq. 10% HCl (39 mL) and H$_2$O (408 mL), then extracted with DCM (400 mL, then 3×300 mL). The combined organic phases were washed with brine (500 mL), dried over Na$_2$SO$_4$ and evaporated under reduced pressure to afford 2-methyl-4-(6-(methylthio)-1H-pyrazolo[3,4-d]pyrimidin-3-yl)morpholine (compound 11) (2.58 g, 68% yield) that was used in the next step without further purification.

MS (+ve ion electrospray): m/z 266 [MH$^+$]

(a) 2-methyl-4-(6-(methylsulfonyl)-1-(tetrahydro-2H-pyran-2-yl)-1H-pyrazolo[3,4-d]pyrimidin-3-yl) morpholine (Compound 12, Wherein Pg is THP)

2-methyl-4-(6-(methylthio)-1H-pyrazolo[3,4-d]pyrimidin-3-yl)morpholine (compound 11) (2.58 g, 9.72 mmol) was dissolved in THF (100 mL). 3,4-dihydro-2H-pyran (3.55 mL, 38.9 mmol) was added followed by p-toluenesulfonic acid monohydrate (185 mg, 0.1 eq, 0.97 mmol). The resulting mixture stirred at 65° C. overnight. Half the solvent was evaporated under vacuum, where the reaction mixture partitioned between EtOAc and sat. aq. sol. NaHCO$_3$. The aqueous layer was extracted with EtOAc (4×). The combined organic layers were washed with brine, dried over Na$_2$SO$_4$ and the solvent removed under vacuum to afford a solid residue that was triturated with Et$_2$O to give 2-methyl-4-(6-(methylthio)-1-(tetrahydro-2H-pyran-2-yl)-1H-pyrazolo[3,4-d]pyrimidin-3-yl)morpholine (12a, wherein Pg is THP) as a pale solid (2.7 g, 79% yield).

MS (+ve ion electrospray): m/z 350 [MH$^+$]

To a stirred solution of 2-methyl-4-(6-(methylthio)-1-(tetrahydro-2H-pyran-2-yl)-1H-pyrazolo[3,4-d]pyrimidin-3-yl)morpholine (12a, wherein Pg is THP) (2.55 g, 7.3 mmol) in EtOH/H$_2$O (5/1, 80 mL), ammonium molybdate (86 mg, 0.44 mmol) and hydrogen peroxide (1.24 mL, 50% w/w) were added. The reaction was stirred for 6 h and quenched by addition of sat. aq. sol. NaHSO$_3$ (600 mL) and EtOAc (600 mL). The aqueous layers were extracted with EtOAc (3×400 mL) and the combined organic layers were dried under vaccumn to give 2-methyl-4-(6-(methylsulfonyl)-1-(tetrahydro-2H-pyran-2-yl)-1H-pyrazolo[3,4-d]pyrimidin-3-yl)morpholine (compound 12, wherein Pg is THP) (2.86 g, quant. yield) which used in the next step without purifying.

MS (+ve ion electrospray): m/z 382 [MH$^+$]

(b) 3,3,3-trifluoro-N-((1,4-trans)-4-((3-(2-methyl-morpholino)-1-(tetrahydro-2H-pyran-2-yl)-1H-pyrazolo[3,4-d]pyrimidin-6-yl)amino)cyclohexyl)propane-1-sulfonamide (Compound 13, Wherein Pg is THP)

DIPEA (4.33 mL, 24.85 mmol) was added to a stirred solution of 2-methyl-4-(6-(methylsulfonyl)-1-(tetrahydro-2H-pyran-2-yl)-1H-pyrazolo[3,4-d]pyrimidin-3-yl)morpholine (compound 12, wherein Pg is THP) (2.37 g, 6.21 mmol) and Intermediate A (3.14 g, 8.07 mmol) in DMSO (62 mL). The mixture was heated to 100° C. and stirred for 2 days, then partitioned between Et$_2$O and H$_2$O. The aqueous phase was washed with Et$_2$O (2×). The combined organics were washed with brine, dried over Na$_2$SO$_4$ and concentrated under vacuum to give crude material which was purified by flash column chromatography (Cyclohexane/EtOAc/MeOH 60/30/10) to afford 3,3,3-trifluoro-N-((1,4-trans)-4-((3-(2-methylmorpholino)-1-(tetrahydro-2H-pyran-2-yl)-1H-pyrazolo[3,4-d]pyrimidin-6-yl)amino)cyclohexyl)propane-1-sulfonamide (compound 13, wherein Pg is THP) (2.15 g, 60% yield).

MS (+ve ion electrospray): m/z 576 [MH$^+$]

It will be appreciated by the skilled artisan that the above reaction may be carried out using 2-methylmorpholine hydrochloride salt (Intermediate B, hydrochloride salt) since more than one equivalent of base (DIPEA) is employed.

(c) 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Formula I)

3,3,3-trifluoro-N-((1,4-trans)-4-((3-(2-methylmorpholino)-1-(tetrahydro-2H-pyran-2-yl)-1H-pyrazolo[3,4-d]pyrimidin-6-yl)amino)cyclohexyl)propane-1-sulfonamide (compound 13, wherein Pg is THP) (2.15 g, 3.73 mmol) was added to 1.25 M HCl in MeOH (15 mL) and the reaction stirred at 65° C. for 1 h. The mixture was concentrate under vacuum and partitioned between H$_2$O and EtOAc. The organic phase was washed with brine, dried over Na$_2$SO$_4$ and evaporated under vacuum to give crude material which was purified by flash coluumn chromatography (DCM/EtOAc/MeOH 75/20/5) to afford a racemic mixture of the compound of Formula I and its opposite enantiomer (Formula Ia) (1.48 g, 81% yield of racemate).

The single enantiomers of racemic mixture Formula Ia were obtained by chiral separation using preparative chiral HPLC: Enantiomer 1 (439 mg, ee>99%, 24% yield) and Enantiomer 2 (414 mg, ee>99%, 23% yield, desired product). The enantiomeric excess of the enantioenriched material thusobtained was determined by chiral HPLC according to the following analytical method: 250 mm Chiralpak IA, 5 mm i.D., EtOH/MeOH/DCM=45/45/10+0.1% Isopropanol, 1 mL/min, 220 nm. Enantiomer 1, Rt=7.7 min; Enantiomer 2, Rt=11.7 min.

Characterisation of Enantiomer 2 (compound of Formula I)

$^1$H NMR (500 MHz, CDCl$_3$) δ11.93 (1H, br s), 8.85 (1H, br s), 7.37 (1H, d), 7.18 (1H, br s), 3.88 (1H, dd), 3.78-3.56 (5H, m), 3.34-3.24 (2H, m), 3.18 (1H, br s), 2.91-2.82 (1H, m), 2.76-2.60 (2H, m), 2.59-2.49 (1H, m), 2.02-1.87 (4H, m), 1.42-1.28 (4H, m) and 1.17 (3H, d).

MS (+ve ion electrospray): m/z 492 [MH$^+$]

Example 1 Method C (a) (2,4-dichloropyrimidin-5-yl)[(S)(2-methylmorpholino)]methanone (Compound 3* [Compound 3, (S) enantiomer])

Phosphorus pentachloride (1190 g, 5.70 mol, sinoreagent) was added portionwise to a suspension of 2,4-dihydroxypyrimidine-5-carboxylic acid (compound 1) (254 g, 1.6 mol, Shanghai Bide) in phosphorous oxychloride (2 Kg, 13.02 mol, Qingxian Keruixi) at 25° C. The reaction mixture was heated to 115° C. and stirred for 16 h. The reaction was cooled to 27° C. and the volatiles were removed under vacuum to provide a yellow semi-solid. Petroleum ether (700 mL) was added to the crude product where precipitation occurred. The mixture was filtered and the filter cake was washed with petroleumm ether (200 mL). The filtrate was evaporated under reduced pressure to give 2,4-dichloropyrimidine-5-carbonyl chloride (compound 2) as a yellow oil (268 g, 78% yield). This material was used in the next step without further purification.

A solution of (S)-2-methylmorpholine (Intermediate B*) (141 g, 1.39 mol, Shanghai Shuya) and TEA (141.1 g, 1.4 mol, Tianjin Fuchen) in DCM (1000 mL) was added dropwise to a stirred solution of 2,4-dichloropyrimidine-5-carbonyl chloride (compound 2) (268 g, 1.3 mol) in dry DCM (3000 mL) at 0° C. under N$_2$. The reaction mixture was stirred for 3 h at 0° C. and then quenched with H$_2$O (500 mL). The phases were separated and the aqueous phase was extracted with DCM (2×300 mL). The combined organic phases were washed with 0.5 M HCl (1000 mL), brine (2000 mL), dried over Na$_2$SO$_4$ and then evaporated under reduced pressure. The residue was purified by flash column chromatography (petroleum/EtOAc 20/1 to 1/1) to give desired (2,4-dichloropyrimidin-5-yl)[(S)(2-methylmorpholino)]methanone (compound 3*) as a yellow oil (188 g, 53% yield).

$^1$H NMR (400 MHz, DMSO-d$_6$) δ: 8.86 (1H, s), 4.33-4.25 (1H, m), 3.95-3.68 (1H, m), 3.58-3.37 (3H, m), 3.17-2.64 (2H, m), 1.20-0.98 (3H, m).

(b) 3,3,3-trifluoro-N-((1,4-trans)-4-((4-methoxy-5-[(S)-(2-methylmorpholine-4-carbonyl)]pyrimidin-2-yl)amino)cyclohexyl)propane-1-sulfonamide (Compound 5* [Compound 5, (S) enantiomer]

Sodium methoxide (40.5 g, 748.9 mmol, Beijing Feilongrui) was added in portions to a stirred solution of (S)-(2, 4-dichloropyrimidin-5-yl)(2-methylmorpholino)methanone (compound 3*) (188 g, 680.9 mmol) in dry THF (2 L) at −40° C. under N$_2$. The reaction mixture was stirred for 1 h at −40° C. and further sodium methoxide (9.2 g) was added in one portion. The reaction mixture was stirred at −40° C. for 1 h and then, gradually warmed to −10° C. for 1 h. The reaction mixture was quenched with sat. aq. sol. ammonium chloride solution (500 mL) at 5-10° C. and extracted with EtOAc (3×500 mL). The combined organic phases were washed with brine (1000 mL), dried over Na$_2$SO$_4$ and evaporated under reduced pressure. The resulting crude material was purified by flash column chromatography (petroleum ether/EtOAc from 20/1 to 1/1) to give two fractions of (2-chloro-4-methoxypyrimidin-5-yl)[(S)(2-methylmorpholino)]methanone (compound 4* [compound 4, (S) enantiomer]) (75 g, 38% yield and 30 g, 14% yield) as a yellow oil. This material was used in the next step without further purification.

To a solution of (2-chloro-4-methoxypyrimidin-5-yl)[(S)-(2-methylmorpholino)]methanone (compound 4*) (75 g, 276 mmol) in dry dioxane (1500 mL) was added DIPEA (178.4 g, 1.4 mol, Beijing Feilongrui) and N-((1,4-trans)-4-aminocyclohexyl)-3,3,3-trifluoropropane-1-sulfonamide, TFA salt (Intermediate A, TFA salt) (139.4 g, 358.8 mmol) in one portion at 27° C. The resulting mixture was stirred at 120° C. for 16 h. The mixture was cooled to 20° C., where water (800 mL) and EtOAc (500 mL) were added. The reaction mixture was stirred for 10 min; then, the organic phase was sepered and the aqueous layer was extracted with more EtOAc (2×500 mL). The combined organic phases were washed with brine (2000 mL), dried over Na$_2$SO$_4$ and filtered. The solvent was removed under vacuum to afford crude material which was purified by flash column chromatography (DCM/MeOH 50/1 to 20/1) to afford 3,3,3-trifluoro-N-((1,4-trans)-4-((4-methoxy-5-[(S)-(2-methylmorpholine-4-carbonyl)]pyrimidin-2-yl)amino)cyclohexyl)propane-1-sulfonamide (compound 5*) (100 g, 71% yield) as a pale solid.

$^1$H NMR (400 MHz, DMSO-d$_6$ δ: 8.03 (1H, s), 7.49-7.31 (2H, m), 3.91-3.60 (5H, m), 3.48-3.11 (9H, m), 2.68-2.62 (2H, m), 1.98-1.96 (4H, m), 1.43-1.29 (4H, m), 1.16-1.01 (3H, s).

(c) 3,3,3-trifluoro-N-((1,4-trans)-4-((4-methoxy-5-[(S)-(2-methylmorpholine-4-carbonothioyl)]pyrimidin-2-yl)amino)cyclohexyl)propane-1-sulfonamide (Compound 6* [Compound 6, (S) enantiomer])

3,3,3-trifluoro-N-((1,4-trans)-4-((4-methoxy-5-[(S)-(2-methylmorpholine-4-carbonyl)]pyrimidin-2-yl)amino)cyclohexyl)propane-1-sulfonamide (compound 5*) (117 g, 229.6 mmol) was dissolved in dry THF (1700 mL). Lawesson's reagent (162.5 g, 401.8 mmol, Qingxian Keruixi) was added in portions and the resulting mixture was stirred for 2 h at 45° C. The reaction mixture was cooled to 25° C. and quenched by addition of sat. aq. sol. NaHCO$_3$ (800 mL). The reaction mixture was stirred for 10 min at RT and then extracted with EtOAc (3×500 mL). The combined organic phases were washed with brine (1000 mL) and dried over Na$_2$SO$_4$. The solvent was removed under vacuum to afford a crude product which was purified by flash column chromatography (DCM/MeOH 100/1 to 20/1) to afford 3,3,3-trifluoro-N-((1,4-trans)-4-((4-methoxy-5-[(S)-(2-methylmorpholine-4-carbonothioyl)]pyrimidin-2-yl)amino)cyclohexyl)propane-1-sulfonamide (compound 6*) (91 g, 74% yield) as a green solid.

$^1$H NMR (400 MHz, DMSO-d$_6$) δ: 8.11-8.04 (1H, m), 7.48-7.31 (2H, m), 5.34-5.11 (1H, m), 3.96-2.84 (13H, m), 2.73-2.59 (2H, m), 2.00-1.78 (4H, m), 1.44-1.27 (4H, s), 1.21-1.02 (3H, m).

(d) 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Formula I)

3,3,3-trifluoro-N-((1,4-trans)-4-((4-methoxy-5-[(S)-(2-methylmorpholine-4-carbonothioyl)]pyrimidin-2-yl)amino)cyclohexyl)propane-1-sulfonamide (compound 6*) (91 g, 173.1 mmol, Beijing Innochem) was dissolved in dioxane (1200 mL), then hydrazine hydrate 85% (173.2 g, 3.5 mol) was added and the reaction stirred at 90° C. for 18 hours. The mixture was cooled to 25° C., where H$_2$O (800 mL) and EtOAc (800 mL) were added and the mixture was stirred at 25° C. for 20 min. The organic phase was separated and the aqueous phase was extracted with EtOAc (3×1500 mL). The combined organic phases were washed with brine (2×2000 mL) and dried over Na$_2$SO$_4$. The solvent was removed under vacuum and EtOAc (400 mL) was added to the residue and stirred at 27° C. for 1 hour. The resulting mixture was filtered, the cake was washed with EtOAc (100 mL) and the filtrate was dried in vacuo to afford a crude solid. This solid was then purified by re-crystallization from methanol (400 mL) to give 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Formula I) (40 g, 47%) as a light green solid.

$^1$H NMR (400 MHz, DMSO-d$_6$) δ: 11.93 (1H, s), 8.82 (1H, s), 7.33 (1H, d), 7.14 (1H, s), 3.86 (1H, dd), 3.73-3.55 (5H, m), 3.31-3.09 (3H, m), 2.90-2.81 (1H, m), 2.66-2.50 (3H, m), 1.92 (4H, s br), 1.39-1.29 (4H, m), 1.15 (3H, d).

Example 2

2-(phosphonooxy)ethyl 3-((S)-2-methylmorpholino)-6-(((1,4-trans)-4-(3,3,3-trifluoropropylsulfonamido)cyclohexyl)amino)-1H-pyrazolo[3,4-d]pyrimidine-1-carboxylate or 2-(phosphonooxy)ethyl 3-((S)-2-methylmorpholino)-6-(((1,4-trans)-4-(3,3,3-trifluoropropylsulfonamido)cyclohexyl)amino)-2H-pyrazolo[3,4-d]pyrimidine-2-carboxylate

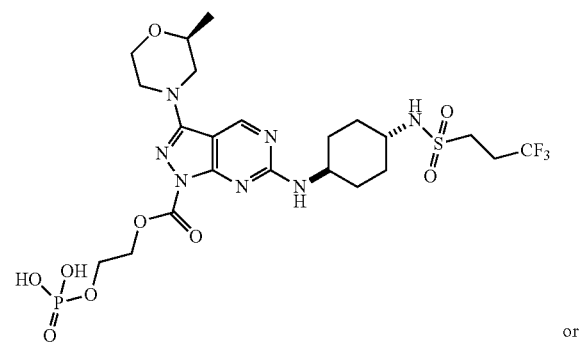

or

-continued

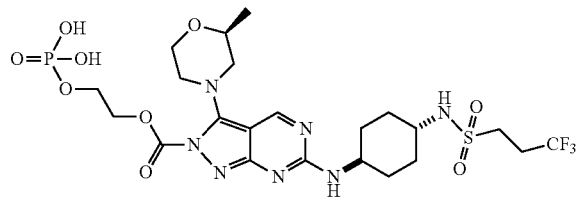

(a) 2-((di-tert-butoxyphosphoryl)oxy)ethyl 3-((S)-2-methylmorpholino)-6-(((1,4-trans)-4-(3,3,3-trifluoropropylsulfonamido)cyclohexyl)amino)-1H-pyrazolo[3,4-d]pyrimidine-1-carboxylate or 2-((di-tert-butoxyphosphoryl)oxy)ethyl 3-((S)-2-methylmorpholino)-6-(((1,4-trans)-4-(3,3,3-trifluoropropylsulfonamido)cyclohexyl)amino)-2H-pyrazolo[3,4-d]pyrimidine-2-carboxylate i) Sodium hydride, 60% dispersion in mineral oil (0.818 g, 20.45 mmol) was added to a mixture of 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Example 1) (6.7 g, 13.63 mmol) in DMF (160 mL). The reaction mixture was stirred at RT for 20 min. After this time 2-((di-tert-butoxyphosphoryl)oxy)ethyl (2,5-dioxopyrrolidin-1-yl) carbonate (Intermediate C) (8.08 g, 20.45 mmol) was added to the mixture and it was heated to 60° C. overnight.

This reaction mixture was combined with other batches of crude material obtained using the same procedure as (i), each procedure respectively starting from 1 g, 1 g, 7.7 g and 6.7 g of 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide (Example 1). The mixture of batches were poured into water (400 mL) and extracted with EtOAc (500 mL). The organic layer was washed with water (2×200 mL), dried over Na$_2$SO$_4$, filtered and evaporated under reduced pressure. The residue was purified by flash column chromatography (0-50% EtOH:EtOAc (1:3)/cyclohexane) to afford a pale yellow solid.

This batch was re-purified by flash column cromatography (0-3% MeOH/DCM) to give desired 2-((di-tert-butoxyphosphoryl)oxy)ethyl 3-((S)-2-methylmorpholino)-6-(((1,4-trans)-4-(3,3,3-trifluoropropylsulfonamido)cyclohexyl)amino)-1H-pyrazolo[3,4-d]pyrimidine-1-carboxylate or 2-((di-tert-butoxyphosphoryl)oxy)ethyl 3-((S)-2-methylmorpholino)-6-(((1,4-trans)-4-(3,3,3-trifluoropropylsulfonamido)cyclohexyl)amino)-2H-pyrazolo[3,4-d]pyrimidine-2-carboxylate as a white solid (15.2 g, 60% global yield)

$^1$H NMR (400 MHz, DMSO-d$_6$) δ: 9.09-8.94 (1H, m), 7.82-7.63 (1H, m), 7.36 (1H, d), 4.59-4.46 (2H, m), 4.23-4.11 (2H, m), 3.93-3.61 (6H, m), 3.34-3.25 (2H, m), 3.22-3.10 (1H, m), 3.03-2.91 (1H, m), 2.72-2.58 (3H, m), 2.02-1.87 (4H, m), 1.45-1.31 (22H, m) and 1.16 (3H, d)

(b) 2-(phosphonooxy)ethyl 3-((S)-2-methylmorpholino)-6-(((1,4-trans)-4-(3,3,3-trifluoropropylsulfonamido)cyclohexyl)amino)-1H-pyrazolo[3,4-d]pyrimidine-1-carboxylate or 2-(phosphonooxy)ethyl 3-((S)-2-methylmorpholino)-6-(((1,4-trans)-4-(3,3,3-trifluoropropylsulfonamido)cyclohexyl)amino)-2H-pyrazolo[3,4-d]pyrimidine-2-carboxylate Example 2

2 N HCl in Et$_2$O (89 mL, 178 mmol) was dropwise added (addition time=20 min) to a 0° C. cooled mixture of 2-((di-tert-butoxyphosphoryl)oxy)ethyl 3-((S)-2-methylmorpholino)-6-(((1,4-trans)-4-(3,3,3-trifluoropropylsulfonamido)cyclohexyl)amino)-1H-pyrazolo[3,4-d]pyrimidine-1-carboxylate (13.75 g, 17.82 mmol) in DCM (200 mL). The resulting mixture was gradually warmed to RT and stirred overnight at RT.

The resulting suspension was filtered, and the solids were collected and washed with DCM (2×25 mL) to give a pale yellow solid.

This solid was dissolved in MeOH (500 mL) and concentrated to about ½ its volume and then, acetone (150 mL) was added to the solution. A precipitate was obtained and the solid was collected by filtration to afford a pale yellow solid.

This solid was dissolved in MeOH (500 mL) and concentrated to about ½ its volume and then EtOAc (150 mL) was added to the solution. A precipitate was obtained and the solid was collected by filtration to afford 2-(phosphonooxy)ethyl 3-((S)-2-methylmorpholino)-6-(((1,4-trans)-4-(3,3,3-trifluoropropylsulfonamido)cyclohexyl)amino)-1H-pyrazolo[3,4-d]pyrimidine-1-carboxylate or 2-(phosphonooxy)ethyl 3-((S)-2-methylmorpholino)-6-(((1,4-trans)-4-(3,3,3-trifluoropropylsulfonamido)cyclohexyl)amino)-2H-pyrazolo[3,4-d]pyrimidine-2-carboxylate (Example 2) (5.45 g, 46%) as a pale yellow solid.

$^1$H NMR (400 MHz, DMSO-d$_6$) δ: 9.08-8.96 (1H, m), 7.88-7.62 (1H, m), 7.40-7.26 (1H, m), 7.02-5.95 (2H, br s), 4.55-4.42 (2H, m), 4.22-4.09 (2H, m), 3.95-3.60 (6H, m), 3.34-3.24 (2H, m), 3.22-3.09 (1H, m), 3.03-2.92 (1H, m), 2.73-2.58 (3H, m), 2.01-1.84 (4H, m), 1.49-1.27 (4H, m) and 1.17 (3H, d)

Biological Activity

Intra macrophage Leishmania donovani assay

The intramacrophage Leishmania assay was performed exactly as described in de Rycker et al (Antimicrob Agents Chemother. 2013 July; 57(7):2913-22. doi: 10.1128/AAC.02398-12. Epub 2013 Apr. 9. Comparison of a high-throughput high-content intracellular Leishmania donovani assay with an axenic amastigote assay. De Rycker M, Hallyburton I, Thomas J, Campbell L, Wyllie S, Joshi D, Cameron S, Gilbert I H, Wyatt P G, Frearson J A, Fairlamb A H, Gray D W.). Briefly, 1 µl of compound was pre-dispensed into 384 well sterile intermediary plates. For single point screening, amphotericin B was added to all wells of column 24 as a positive control (final concentration 2 µM) and DMSO to column 23. For potency determinations, ten-point, one in three dilution curves were created with the highest concentration being 50 µM and on each plate a control curve of amphotericin B was included. Controls were as follows: columns 11 and 12: DMSO, columns 23 and 24: amphotericin B (final concentration 2 µM). To the intermediary plates, 100 µl of THP-1 media was added and plates were shaken for >5 min to ensure complete mixing. THP-1 cells (8,000 per well, 50 μl) were plated into black clear-bottom 384 well plates (Corning) in presence of 10 nM PMA. After 20 min at RT, the plates were incubated at 37° C. under 5% $CO_2$ in a humidified incubator for 75 h. The cells were then washed with 450 μl sterile phosphate buffered saline (PBS) supplemented with 1 mM $CaCl_2$, 0.5 mM $MgCl_2$, 0.1% (w/v) bovine serum albumin (PBS-A) and amastigotes were added to all wells at a multiplicity of infection of 5 (40,000 amastigotes per well). After 40 min at RT, plates were returned to the incubator. Amastigotes were incubated in the presence of macrophages for 16 h. Any remaining extracellular amastigotes were subsequently removed with an overflow wash of 1 mL PBS-A per well (wash buffer is being aspirated from the top of the well as it is being dispensed) followed by addition of 25 μl of the compound pre-dilutions using a Matrix Hydra DT pipetting station. The final dilution of each compound was 200-fold. Plates were incubated for 72 h and then washed (250 μl PBS-A) and fixed (4% (v/v) formaldehyde-PBS, 30 min, RT). After fixation, the wells were washed with 250 μl PBS, stained (10 μg/mL DAPI, 0.4 μg mL-1 HCS Cellmask Deep Red in PBS+0.1% (v/v) Triton X-100, 30 min, RT) and washed with 250 μl PBS. Finally, PBS+0.05% (v/v) thimerosal was added to the wells, the plates were sealed and imaged on a high-content microscope (GE IN Cell 1000 or GE IN Cell 2000) using a 10× objective. Image analysis was carried out with GE IN Cell Analyzer 1000 Workstation using the "Multi Target Analysis" module. Settings for segmentation were as follows: nuclei: minimum area: 142.384 $\mu m^2$, sensitivity: 81, method: top-hat; cells: characteristic area: 2500 $\mu m^2$, sensitivity: 60, method: multiscale top-hat; organelles (amastigotes): granule size 1-3, 3 scales, sensitivity: 90, detection in entire cell. For each well, i) THP-1 cell count (cytotoxicity readout) and ii) average number of amastigotes per cell (potency readout) were calculated, both in terms of $pEC_{50}$ values.

Results of the Intramacrophage Leishmania donovani assay

The compound of Formula (I), its opposite enantiomer and the racemic mixture of both were each tested in the Intramacrophage Leishmania donovani assay.

The compound of Formula (I), its opposite enantiomer and the racemic mixture of both (Formula 1a) are found to have a $pEC_{50}$ value of 5.3 or more against amastigotes and $pEC_{50}$ value of 4.4 or less against THP-1 cells in the Intramacrophage Leishmania donovani assay. For example, the compound of Formula (I) is found to have a $pEC_{50}$ value of 6.0 against amastigotes and $pEC_{50}$ value of 4.3 against THP-1 cells in the Intramacrophage Leishmania donovani assay.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. The compound 3,3,3-trifluoro-N-((1,4-trans)-4-((3-((S)-2-methylmorpholino)-1H-pyrazolo[3,4-d]pyrimidin-6-yl)amino)cyclohexyl)propane-1-sulfonamide, having the Formula (I):

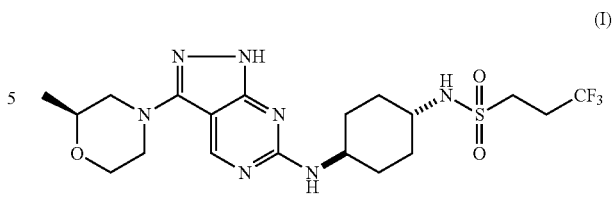

or a salt thereof.

2. The compound of Formula (I) according to claim 1, or a pharmaceutically acceptable salt thereof.

3. The compound of Formula (I) according to claim 1, having the Formula (I):

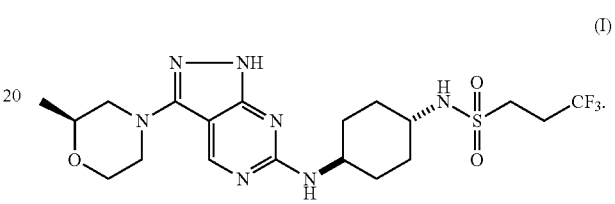

4. A pharmaceutical composition comprising a compound of Formula (I) according to claim 2, or a pharmaceutically acceptable salt thereof, together with at least one pharmaceutically acceptable carrier.

5. A combination comprising (a) a compound of Formula (I) according to claim 2, or a pharmaceutically acceptable salt thereof, and (b) at least one additional anti-leishmaniasis agent selected from the group consisting of miltefosine, paromomycin, sodium stibugluconate, meglumine antimoniate, amphotericin B deoxycholate, and liposomal amphotericin B.

6. A method of treatment of leishmaniasis, which method comprises administering to a mammal in need thereof, a therapeutically effective amount of a compound of Formula (I) according to claim 2, or a pharmaceutically acceptable salt thereof.

7. A method of treatment according to claim 6, wherein the mammal is a human.

8. A method of treatment according to claim 6, wherein the leishmaniasis is visceral leishmaniasis.

9. The compound which is 3,3,3-trifluoro-N-((1,4-trans)-4-((3-((R)-2-methylmorpholino)-1H-pyrazolo[3,4-d]pyrimidin-6-yl)amino)cyclohexyl)propane-1-sulfonamide:

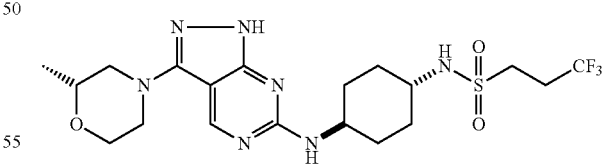

or a salt thereof.

10. A mixture comprising (a) a compound of Formula (I) according to claim 1, or a salt thereof, and (b) the opposite enantiomer of a compound of Formula (I) which is 3,3,3-trifluoro-N-((1,4-trans)-4-(((3-((R)-2-methylmorpholino)-1H-pyrazolo[3,4-d]pyrimidin-6-yl)amino)cyclohexyl)propane-1-sulfonamide, or a salt thereof.

11. A pharmaceutical composition comprising a compound of Formula (I) according to claim 3, together with at least one pharmaceutically acceptable carrier.

12. A combination comprising (a) a compound of Formula (I) according to claim 3, and (b) at least one additional anti-leishmaniasis agent selected from the group consisting of miltefosine, paromomycin, sodium stibugluconate, meglumine antimoniate, amphotericin B deoxycholate, and liposomal amphotericin B.

13. A method of treatment of leishmaniasis, which method comprises administering to a mammal in need thereof, a therapeutically effective amount of a compound of Formula (I) according to claim 3.

14. A method of treatment according to claim 13, wherein the leishmaniasis is visceral leishmaniasis.

15. A method of treatment according to claim 13, wherein the mammal is a human.

\* \* \* \* \*